US011060069B2

(12) United States Patent
Jordan et al.

(10) Patent No.: US 11,060,069 B2
(45) Date of Patent: Jul. 13, 2021

(54) PORCINE CELL LINE FOR VIRUS PRODUCTION

(71) Applicant: ProBioGen AG, Berlin (DE)

(72) Inventors: Ingo Jordan, Berlin (DE); Volker Sandig, Berlin (DE); Deborah Horn, Berlin (DE); Katrin John, Berlin (DE)

(73) Assignee: Probiogen AB, Berlin (DE)

( * ) Notice: Subject to any disclaimer, the term of this patent is extended or adjusted under 35 U.S.C. 154(b) by 0 days.

(21) Appl. No.: 16/348,086

(22) PCT Filed: Nov. 9, 2016

(86) PCT No.: PCT/EP2016/077171
§ 371 (c)(1),
(2) Date: May 7, 2019

(87) PCT Pub. No.: WO2018/086686
PCT Pub. Date: May 17, 2018

(65) Prior Publication Data
US 2019/0300863 A1 Oct. 3, 2019

(51) Int. Cl.
*C12N 7/00* (2006.01)
*C12N 5/071* (2010.01)
*C12N 5/16* (2006.01)

(52) U.S. Cl.
CPC ............ *C12N 7/00* (2013.01); *C12N 5/0686* (2013.01); *C12N 5/16* (2013.01); *C12N 2510/02* (2013.01); *C12N 2760/16151* (2013.01)

(58) Field of Classification Search
None
See application file for complete search history.

(56) References Cited

U.S. PATENT DOCUMENTS

| | | | | |
|---|---|---|---|---|
| 4,335,105 A | * | 6/1982 | Gough | A61K 39/225 424/157.1 |
| 2013/0336927 A1 | | 12/2013 | Nauwynck | |
| 2019/0300863 A1 | * | 10/2019 | Jordan | C12N 7/00 |

FOREIGN PATENT DOCUMENTS

WO 2009/059411 A1 5/2009

OTHER PUBLICATIONS

Sakoda et al. (Journal of Virological Methods. 1998; 75: 59-68).*
Lamp et al. (Journal of Virology. 2013; 87 (21): 11872-11883).*
Chen et al. Derwent abstract of CN_104278009 Sep. 2014.*
Chen et al. Derwent abstract of CN102453698 May 2012.*
Kinder, ("Pneumovirus Infections: Understanding RSV and HMPV Entry, Replication, and Spread." (2020) Theses and Dissertations—Molecular and Cellular Biochemistry; UKnowledge (48) University of Kentucky).*
Sreenivasan et al. (Virology. 2019; 528: 152-163).*

(Continued)

*Primary Examiner* — Shanon A. Foley
(74) *Attorney, Agent, or Firm* — Kilpatrick Townsend & Stockton LLP

(57) ABSTRACT

The present invention relates to a continuous porcine cell line that is capable of proliferating in medium free of animal-derived components. Further, the present invention relates to a method for producing a virus using said cell line and a virus obtainable by said method. Furthermore, the present invention relates to a method for accumulating a virus from an environmental sample using said cell line and a virus obtainable by said method.

17 Claims, 6 Drawing Sheets

Specification includes a Sequence Listing.

(56) References Cited

OTHER PUBLICATIONS

International Search Report in PCT/EP2016/077171, dated Feb. 13, 2017.
Genzel, et al. "Continuous cell lines as a production system for influenza vaccines." Expert review of vaccines 8, No. 12 (2009): 1681-1692.
Hull, et al. "The origin and characteristics of a pig kidney cell strain, LLC-PK 1." In vitro 12, No. 10 (1976): 670-677.
Lee, et al. "Generation of a porcine alveolar macrophage cell line for the growth of porcine reproductive and respiratory syndrome virus." Journal of virological methods 163, No. 2 (2010): 410-415.
Li, et al. "Differential susceptibility of different cell lines to swine-origin influenza A H1N1, seasonal human influenza A H1N1, and avian influenza A H5N1 viruses." Journal of Clinical Virology 46, No. 4 (2009): 325-330.
Seo, et al. "Characterization of a porcine lung epithelial cell line suitable for influenza virus studies." Journal of virology 75, No. 19 (2001): 9517-9525.
Todaro, et al. "Characterization of a type C virus released from the porcine cell line PK (15)." Virology 58, No. 1 (1974): 65-74.
Van Der Valk, et al. "The humane collection of fetal bovine serum and possibilities for serum-free cell and tissue culture." Toxicology in vitro 18, No. 1 (2004): 1-12.
Van Der Valk, et al. "Optimization of chemically defined cell culture media—replacing fetal bovine serum in mammalian in vitro methods." Toxicology in vitro 24, No. 4 (2010): 1053-1063.
Weingartl, et al. "Continuous porcine cell lines developed from alveolar macrophages: partial characterization and virus susceptibility." Journal of virological methods 104, No. 2 (2002): 203-216.

\* cited by examiner

Figure 6

H5N3 infection in presence of serum ± trypsin

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: MACF1 primer 1

<400> SEQUENCE: 1
ccatctgctg agtataaagt ggtgaa                                         26

<210> SEQ ID NO 2
<211> LENGTH: 20

-continued

<212> TYPE: DNA
<213> ORGANISM: Artificial Sequence
<220> FEATURE:
<223> OTHER INFORMATION: MACF1 primer 2

<400> SEQUENCE: 2
gcctccttct gcttgaagca 20

<210> SEQ ID NO 3
<211> LENGTH: 15
<212> TYPE: DNA
<213> ORGANISM: Artificial Sequence
<220> FEATURE:
<223> OTHER INFORMATION: single-primer for amplification of YNZ22 minisatellites

<400> SEQUENCE: 3
ctctgggtgt cgtgc 15

PORCINE CELL LINE FOR VIRUS PRODUCTION

CROSS REFERENCE TO RELATED APPLICATIONS

This application is a U.S. National Stage of PCT/EP2016/077171, international filing date Nov. 9, 2016, the disclosure of which is incorporated herein by reference.

Reference to Submission of a Sequence Listing as a Text File

The Sequence Listing written in file Sequence_Listing_095697-1136024.txt created on May 6, 2019, 4,096 bytes, machine format IBM-PC, MS-Windows operating system, is hereby incorporated by reference in its entirety for all purposes.

The present invention relates to a continuous porcine cell line that is capable of proliferating in medium free of animal-derived components. Further, the present invention relates to a method for producing a virus using said cell line and a virus obtainable by said method. Furthermore, the present invention relates to a method for accumulating a virus from an environmental sample using said cell line and a virus obtainable by said method.

BACKGROUND OF THE INVENTION

Influenza A viruses (AIVs, *Influenzavirus* A genus, Orthomyxoviridae family) have the capacity to both cause acute outbreaks and to establish subclinical presence in poultry and pig farms. They are also known for a high zoonotic and dangerous pandemic potential [1-4]. AIV strains that are usually associated with outbreaks belong into a group consisting of sixteen hemagglutinin (HA, designated as H1-H16) and nine neuraminidase (NA, N1-N9) subtypes [3].

Additional influenza viruses have been discovered recently, those of H17 and H18 subtype that infect bats [5] and influenza D viruses found in ruminants [6]. These, together with influenza B viruses, appear not to be associated with the high pandemic potential of the H1-H16 AIVs.

AIV pathogenicity is determined by a number of factors that range from tropism (for example, viruses that infect the lower respiratory tract tend to cause more severe disease than those that replicate in the upper regions) to interaction with innate immunity (the case fatality rate is higher for strains that induce hypercytokinemia or "cytokine storms") [7,8]. Tropism and host range is mainly determined by the haemagglutinin and neuraminidase proteins (HA and NA, respectively) on the virion surface and the non-structural protein PB2, a subunit of the viral RNA polymerase. Some HA and NA subtypes are more frequently associated with large outbreaks or severe disease (for example, H1N1, H2N2, and H3N2 have caused pandemics in the past, occurrences of H5N1 and H7N9 are currently being closely monitored for dangerous changes in host range) [8,9]. Other strains, such as H9N2, appear to be less virulent but still can be epidemiologically important. For example, H9N2 viruses weaken animals against subsequent secondary bacterial and viral infections [10]. Co-circulating H9N2 viruses are also a concern in China and Egypt because internal (not HA or NA) genes may expand the repertoire of a receiving virus towards higher pathogenic potential [11-14]. This exchange of genes is facilitated because the AIVs distribute their genomic information across eight segments, each a molecule of negative-sense linear single stranded RNA. The viral chromosomes can be re-assorted upon coinfection of animals, especially pigs, that are susceptible to different strains and may yield viruses with profound shifts in virulence, host range and pandemic potential [15].

Poultry exposure is a dominant risk factor for human infections with AIVs [9,16]. AIV infections also cause substantial economic disruptions in poultry and pig farms. They are being controlled by a combination of monitoring, containment strategies, culling of infected animals, and vaccination [17,18]. Vaccination of animals is performed with killed preparations (not live-attenuated viruses) using low pathogenic AIVs (LPAIVs) as production seed [18]. The vaccines are being manufactured in embryonated chicken eggs or in primary chicken embryo fibroblasts. A wide variety of strains have been used to protect against infection with H9N2, H5N2, H5N1, H7N3, H7N7 viruses in various parts of Asia, North America and North Africa [18].

Influenza virus epidemiology is complex due to a combination of properties: (1) Different viral strains can differ in virulence that ranges from unapparent to acute infections. Especially migratory ducks can serve as a mobile reservoir where viruses spill out of apparently healthy flocks into inappropriately secured facilities were pigs or chickens are kept. (2) The genomic information of influenza viruses is organized into distinct RNA segments that can re-assort into novel strains in host cells infected with more than one strain. This allows for rapid shifts of epidemic and pandemic properties. (3) Pigs are especially permissive to influenza viruses of various origins and can accelerate generation of re-assortants. (4) Pig and chicken farming belong to the most dynamic agricultural sectors with huge global populations of animals and extensive exchange of goods, both live animals and potentially contaminated derived products. Chickens and pigs are frequently kept in a proximity suitable for exchange of influenza viruses.

The inventors of the present patent application developed a novel and advantageous continuous porcine cell line that is capable of proliferating in medium free of animal-derived components. This cell line easily allows the accumulation of viruses found in environmental samples. Said cell line has the advantage that it is permissive for a broad virus spectrum that includes influenza A virus, influenza B virus, influenza C virus, and influenza D virus as well as bat-derived strains. High permissivity for viruses such as low pathogenic avian influence viruses (LPAIVs) is a highly desirable property as such virus preparations may serve as emergency vaccines.

Embryonated eggs are traditionally used to isolate influenza viruses and to produce vaccines. Problems that are associated with the current production system are low yields for certain strains so that expensive concentration steps are necessary to increase potency, considerable amounts of egg shells that remain as biohazardous solid waste if vaccines are being produced in egg cavities, and dependence on a continuous supply with embryonated eggs free of adventitious agents [18-20]. Improved control over supply with embryonated eggs is achieved by constructing breeding facilities immediately adjacent to the production site, but this comes at substantial costs [21]. Affordability and supply security may also be affected by dependence on eggs [22]. One third of the total production costs for certain avian vaccines is reported to be incurred by the preparation of the primary chicken cells [23]. Rigid intervals between husbandry, harvest of eggs and inoculation with vaccine seed must be accommodated [24] and there is an elevated risk of contamination with environmental and endogenous agents [20,25,26]. The strain on resources is only partially mitigated even if vaccines are produced with embryonated eggs from apparently healthy flocks instead of flocks of the more expensive Specific Pathogen Free status. Especially the wide spectrum of *mycoplasma* that can infect and be endemic in poultry, and that may not be uniformly sensitive to common inactivation procedures, can complicate the vaccine production with embryonated eggs of lesser defined health status [27].

The MDCK cell line complements embryonated eggs in influenza virus research and vaccine production. Stewart Madin and Norman Darby established this continuous cell line from primary kidney cells of an adult cocker spaniel in 1958. Some MDCK cell lineages are highly permissive for diverse strains of influenza virus A or influenza virus B. MDCK-based production processes for killed vaccines against seasonal influenza have been developed based on this combination of properties. The first regulatory approval for a trivalent subunit vaccine against flu produced in MDCK cultures (OPTAFLU, Novartis) was granted in 2007 [28, 29].

As efficient as embryonated eggs and MDCK cells may be for propagation of many influenza viruses, several virus isolates do not replicate at all, or not to levels required for vaccine production in the traditional systems [4,30]. Viral strains derived from pigs are known to have the capacity to cause pandemic outbreaks of disease [31] so that a novel cell substrate derived from pigs, with natural permissivity for the pig-derived viruses, may improve vaccine supply security. In addition, the canine MDCK cell line is derived from a species that is not epidemiologically relevant for virus pandemics such as influenza virus pandemics.

Another problem concerning vaccines such as influenza vaccines is that a mismatch between antigens contained in a vaccine and antigens displayed by circulating viruses can severely reduce vaccine efficacy [32]. How much a given strain present in current vaccines may predominate virus activity such as influenza activity in the future is very difficult to predict and one source for vaccine mismatch.

Vaccine mismatch can also occur if a correctly selected seasonal strain adapts to the production protocol. The result can be that antigens expressed by the produced virus do not protect against epitopes displayed by circulating strains. Such a detrimental adaptation of influenza viruses to embryonated eggs or MDCK cell substrates has been described previously [32].

Thus, there is a need for a new cell line which does not have the above disadvantages. The inventors of the present patent application developed a novel and advantageous continuous porcine cell line that is capable of proliferating in medium free of animal-derived components. This cell line allows the production of viruses such as influenza viruses in high yields. Said viruses may be used as vaccines. It also relieves the selective pressures on the viruses and, thus, interferes with accumulation of mutations in structural genes.

SUMMARY OF THE INVENTION

In a first aspect, the present invention relates to a continuous porcine cell line that is capable of proliferating in medium free of animal-derived components.

In a second aspect, the present invention relates to a method for producing a virus comprising the steps of:
(i) providing a continuous porcine cell line that is capable of proliferating in medium free of animal-derived components and that is permissive for the virus,
(ii) infecting said cell line with the virus or transfecting said cell line with a plasmid carrying (a) nucleic acid sequence(s) encoding the virus, and
(iii) culturing the cell line infected or transfected in step (ii), thereby producing the virus.

In a third aspect, the present invention relates to a virus obtainable by the method of the second aspect.

In a fourth aspect, the present invention relates to a method for accumulating a virus from an environmental sample comprising the steps of:
(i) providing a continuous porcine cell line that is capable of proliferating in medium free of animal-derived components and that is permissive for a virus,
(ii) contacting said cell line with an environmental sample suspected of containing a virus,
(iii) culturing the cell line contacted in step (ii), thereby accumulating the virus.

In a fifth aspect, the present invention relates to a virus obtainable by the method of the fourth aspect.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU-PAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "virus", as used herein, refers to a small infectious agent that replicates only inside living cells of other organisms. It may also be cultured in cell lines. Viruses can infect all types of life forms, from animals and plants to microorganisms, including bacteria and archaea. While not inside an infected cell or in the process of infecting a cell, viruses exist in the form of independent particles. These viral particles, also known as virions, consist of two or three parts: (i) the genetic material made from either DNA or RNA, long molecules that carry genetic information, (ii) a protein coat, called the capsid, which surrounds and protects the genetic material, and in some cases (iii) an envelope of lipids that surrounds the protein coat when they are outside a cell. The shapes of these virus particles range from simple helical and icosahedral forms for some virus species to more complex structures for others. Thus, the term "virus", as used herein, also encompasses viral particles, particularly infectious particles.

The virus may be a wild-type virus, a mutated virus, a live virus, an inactivated virus, a cold-adapted virus, an attenuated virus (e.g. a highly attenuated virus), or a viral vector. The virus may also be a vaccine/used as vaccine.

The term "inactivated virus", as used herein, refers to a virus grown in culture and then killed, e.g. by using heat or formaldehyde. In contrast, a live virus (which is often an attenuated or cold-adapted virus when used as vaccine) uses pathogens that are still alive (but are almost always attenuated, that is, weakened). Pathogens for inactivated virus vaccines are grown under controlled conditions and are killed as a means to reduce infectivity (virulence) and, thus, prevent infection from the virus vaccine.

The term "cold-adapted virus", as used herein, refers to a virus that has been adapted to grow ideally at 25° C., which means that at normal human or animal body temperature (about 37° C.), it is attenuated. The adaptation process has been shown to have caused stable mutations in the three polymerase genes of the virus, namely PA, PB1, and PB2.

The term "attenuated virus", as used herein, refers to a virus with compromised virulence in the intended recipient, e.g. human or animal recipient. Such a property can be achieved by adaptation of a virus to narrow temperature ranges or narrow host ranges and to other artificial replication environments, including chemically defined media. Replication of such a virus is restricted in cells derived from the intended recipient, e.g. human or animal recipient, or in cells removed from the tissue environment. It may replicate to high titers outside of the intended recipient (e.g. in a permissive cell culture or laboratory animal). An example of an attenuated virus strain is the Ender's attenuated measles virus Edmonston strain given to protect against serious measles disease or the vaccinia virus strain used in the pox eradication campaign of the World Health Organisation (WHO) in the 1970s.

The term "highly attenuated virus", as used herein, refers to a virus with blocked virulence in the intended recipient, e.g. human or animal recipient. Such a property can be achieved by adaptation of a virus to narrow temperature ranges or narrow host ranges and to other artificial replication environments, including chemically defined media. Replication of such a virus is blocked in cells derived from the intended recipient, e.g. human or animal recipient, or in cells removed from the tissue environment. It may replicate to high titers outside of the intended recipient (e.g. in a permissive cell/cell culture or laboratory animal).

The term "virus vaccine", as used herein, refers to an agent that can be used to elicit protective immunity in a recipient, e.g. human or animal recipient. To be effective, a virus vaccine can elicit immunity in a portion of the immunized population, as some individuals may fail to mount a robust or protective immune response or, in some cases, any immune response. This inability may stem from the genetic background of the recipient or because of an immunodeficiency condition (either acquired or congenital) or immunosuppression (e.g., due to treatment with chemotherapy or use of immunosuppressive drugs). Virus vaccine efficacy can be established in animal models.

The term "vaccination", as used herein, means that a specific immunity against viral antigens is induced in a recipient, e.g. human or animal recipient, by mucosal or transdermal exposure with an attenuated infectious virus or by injection of an inactivated form of said virus. After the administration of the vaccine into the body of the recipient, the epitopes are expressed and are presented to the immune system and a specific immune response against these epitopes may be induced. The recipient is, thus, immunized against the protein containing the epitope.

The term "infectious", as used herein, refers to the ability of a virus to replicate in a cell and to produce viral particles. Infectivity can be evaluated, for example, by detecting the virus load or by observing disease progression in a human or in an animal.

The term "pathogenicity", as used herein, refers to the ability of the virus to produce a disease. Viruses may be divided in low pathogenic viruses and highly pathogenic viruses based on the molecular characteristics of the viruses and their ability to cause diseases and mortality.

The term "low pathogenic virus", as used herein, refers to a virus that may cause a mild illness or no disease and may not be detected. Low pathogenic viruses include, but are not limited to, influenza A viruses. A low pathogenic virus may also be designated as lentogenic virus, especially in the context of Newcastle disease virus (NDV).

The term "highly pathogenic virus", as used herein, refers to a virus which causes a severe disease. The signs of the disease are noticeable. It spreads rapidly and may have a high death rate. Highly pathogenic viruses include, but are not limited to, influenza A viruses and Newcastle disease viruses (NDV).

The skilled person can easily distinguish a low pathogenic virus from a highly pathogenic virus. Pathogenicity can be determined in vitro using conventional cell lines that do not contain an endogenous protease. Viruses of low pathogenicity usually require exogenous trypsin for replication. Pathogenicity can also be determined in vivo. One commonly known protocol uses intracerebral inoculation of 1 day-old chicks. The animals are observed for 8 days and scored between 2 (for death) and 0 (without symptoms). The mean score of all measurements is the intracerebral pathogenicity index (ICPI) and should be below 0.7 for live vaccine preparations.

More particularly, the virus may be a negative-sense single stranded RNA ((−) ssRNA) virus, a positive-sense single stranded RNA ((+) ssRNA) virus, a double stranded RNA (dsRNA) virus, a DNA-containing virus such as a double stranded DNA (dsDNA) virus or a single stranded DNA (ssDNA) virus, a single stranded RNA retrovirus (ssRNA-RT virus), or a double stranded DNA reverse transcriptase containing virus (dsDNA-RT virus). Preferably, the negative-sense single stranded RNA ((−) ssRNA) virus is a myxovirus, more preferably a virus of the Orthomyxoviridae or Paramyxoviridae family, the positive-sense single stranded RNA ((+) ssRNA) virus is a virus of the Flaviviridae, Coronaviridae, or Arteriviridae family, the double stranded RNA (dsRNA) virus is a virus of the Reoviridae family, the DNA-containing virus is a virus of the Herpesviridae, Circoviridae, or Asfariviridae family, the single stranded retrovirus (ssRNA-RT virus) is a virus of the Retroviridae family, or the double stranded DNA reverse transcriptase containing virus (dsDNA-RT virus) is a virus of the Hepadnaviridae family. Said virus may be a wild-type virus, a mutated virus, a live virus, an inactivated virus, a cold-adapted virus, an attenuated virus (e.g. a highly attenuated virus), or a viral vector.

The term "influenza virus", as used herein, refers to a virus commonly known to cause infectious diseases (also known as "the flu"). The symptoms can be mild to severe. The most common symptoms include: a high fever, runny nose, sore throat, muscle pains, headache, coughing, and feeling tired. Three types of influenza viruses affect people, called Type A, Type B, and Type C.

The term "New castle disease virus (NDV)", as used herein, refers to a virus commonly known to cause a bird disease affecting many domestic and wild avian species. The virus is transmissible to humans. Exposure of humans to infected birds (for example in poultry processing plants) can cause mild conjunctivitis and influenza-like symptoms, but the Newcastle disease virus otherwise poses no hazard to human health. Interest in the use of NDV as an anticancer agent has arisen from the ability of NDV to selectively kill human tumor cells with limited toxicity to normal cells.

The term "cell culture", as used herein, refers to a process by which cells are grown under controlled conditions, generally outside of their natural environment. In practice, the term "cell culture" refers to the culturing of cells derived from multicellular organisms, e.g. human or animal cells. In a virus cell culture, the cells are hosts for the viruses.

The term "primary cell culture", as used herein, refers to a cell culture that is derived directly from excised, normal human or animal tissue and cultured either as an explant culture or following dissociation into a single cell suspension by enzyme digestion. Such a culture is initially heterogeneous but later become dominated by fibroblasts. The preparation of primary cultures is labor intensive and they can be maintained in vitro only for a limited period of time. During their limited lifespan, primary cells usually retain many of the differentiated characteristics of the cell in vivo.

The term "cell line", as used herein, refers to a cell culture selected for uniformity from a cell population derived from a usually homogeneous tissue source (e.g. an organ).

The term "continuous cell line", as used herein, refers to a cell culture comprising a single cell type that can be serially propagated in culture for prolonged periods. It has an indefinite lifespan. The cell line of the present invention is a continuous porcine cell line. Said cell line is preferably a kidney cell line or a testis cell line. More preferably, said cell line is a PK-15S or STS cell line.

The term "non-adherent cell line", as used herein, refers to a cell line that is able to survive in a suspension culture without being attached to a surface (e.g. tissue culture plastic carrier or micro-carrier). Said cell line has been modified and/or adapted to be able to survive in a suspension culture without being attached to a surface (e.g. tissue culture plastic carrier or micro-carrier). Said cell line can be grown to a higher density than adherent conditions would allow. It is, thus, more suited for culturing in an industrial scale, e.g. in a bioreactor setting or in an agitated culture, for example, in order to produce viruses such as virus vaccines. To make cells attractive for the production of viruses, the cells have to be adapted to a non-adherent cell culture. Because the original cells would undergo apoptosis under serum-free conditions and/or in the absence of a suitable surface, this adaptation is a prolonged process requiring passaging with diminishing amounts of serum, thereby selecting an irreversibly modified cell population. Alternatively, the term "cell line growing/able to grow in suspension culture" may be used.

In contrast thereto, the term "adherent cell line", as used herein, refers to a cell line which requires a surface (e.g. tissue culture plastic carrier or micro-carrier). Said surface may be coated with extracellular matrix components to increase adhesion properties and provide other signals needed for growth and differentiation. Said cells require periodic passaging, but allow easy visual inspection under inverted microscope. Said cells have to be dissociated enzymatically (e.g. with trypsin). In addition, the growth of adherent cells is limited by surface area, which may limit product yields.

When a cell is defined by the term "permissive" herein, this means that the virus is able to circumvent defenses of the cell and is able to invade the cell, replicate in said cell, and escape from said cell.

Sometimes it is not sufficient to have a permissive cell line. Some cell lines have to be "highly permissive", that is, they must be able to replicate the input virus to economically relevant levels. A natively high permissivity also reduces the selective pressures on the input virus to evolve escape mutants that replicate better than the parental virus.

In contrast thereto, the term "cell line non-permissive for a virus", as used herein, refers to a cell line that does not allow the virus multiplication within it.

The degree of permissivity can be defined using the burst size, that is the number of progeny viruses being produced per input virus. A cell line permissive for a virus, has a burst size above 2. In particular, a cell line permissive for a virus has a burst size above 2 and below 100. A cell line highly permissive for a virus has a burst size of at least 100.

The term "cell line highly susceptible for a virus", as used herein, refers to a cell line that can be productively infected with a very low number of input virus. Input virus is experimentally defined by the multiplicity of infection (MOI), the infectious units being added per cell present in a culture. A high susceptibility is evident if a multiplicity of infection (MOI) of less than 0.1, preferably of less than 0.001, can be used. In contrast thereto, a "cell line (only) susceptible for a virus" has to be infected with a higher number of input virus. In this case, a MOI of equal to or more than 0.1, preferably of equal to or more than 1.0, has to be used.

The porcine cell line of the present invention is highly permissive and/or highly susceptible for a high number of different viruses, e.g. for influenza A virus and Newcastle disease virus.

The term "multiplicity of infection (MOI)", as used herein, refers to the ratio of virus to infect cells as target. For example, when referring to a group of cells inoculated with virus particles, the multiplicity of infection (MOI) is the ratio of the number of virus particles to the number of target cells present in a defined space.

The term "serum-free medium", as used herein, refers to a (growth) medium which is devoid of animal serum (including fractionated serum).

The term "medium free of animal-derived components", as used herein, refers to a (growth) medium devoid of any animal-derived components. Preferably, the medium free of animal derived components is a chemically defined medium.

The term "chemically defined medium", as used herein, refers to a (growth) medium suitable for the in vitro cell culture of cells in which all of the chemical components are known. Standard cell culture media are commonly supplemented with animal serum (such as fetal bovine serum, FBS) as a source of nutrients and other ill-defined factors. The technical disadvantages to using serum include its undefined nature, batch-to-batch variability in composition, and the risk of contamination. The term "chemically defined medium", as used herein, also refers to a (growth) medium without any complex mixtures of biologic components.

There is further a clear distinction between a serum-free medium and a chemically defined medium. A serum-free medium may contain undefined animal-derived products such as serum albumin (purified from blood), hydrolysates, growth factors, hormones, carrier proteins, and attachment factors. These undefined animal-derived products will contain complex contaminants, such as the lipid content of albumin. A serum-free medium may also contain plant or microbial hydrolysates. Such hydrolysates represent complex mixtures of single amino acids or smaller peptides (covalently linked amino acids, such as dipeptides or tripeptides in undefined relative amounts) and trace elements that co-purify with the source material for the hydrolysates. In contrast, chemically defined media require that all of the components must be identified and have their exact concentrations known. Therefore, a chemically defined medium may contain recombinant factors but must be entirely free of animal-derived components and cannot contain either fetal bovine serum, bovine serum albumin, human serum albumin, or hydrolysates.

The term "protease cleavage site", as used herein, refers to a cleavage site carried by a virus. In particular, this cleavage site is required for activation of virus infectivity. The protease cleavage site is part of many viruses which must be proteolytically processed for their activation. More specifically, the virions of many viruses must be proteolytically processed for activation of their infectious units. In other words, the structural proteins of the infectious virus particles require a proteolytic processing step at their protease cleavage sites for activation of virus infectivity. This processing in a natural infection situation is mediated by host proteases (e.g. present in the human or animal host) directed against the protease cleavage sites in structural proteins, e.g. the cleavage site in the hemagglutinin protein (HA) of influenza viruses [33-35] or in the F protein of Newcastle disease viruses. For example, the ability of the HA protein of influenza viruses to mediate fusion between viral and endosomal membranes during virus entry into the cell depends on cleavage of fusion-incompetent precursor HA0 into disulfide-linked subunits HA1 and HA2 by a host protease. Cleavage of HA is essential for infection and determines viral pathogenicity and tissue tropism. In addition, the cleavage of the precursor protein F0 into F1 and F2 by host cell proteases is essential for progeny Newcastle disease virus to become infective.

The proteases which are contained in embryonated eggs can, for example, activate myxoviruses. If a cell culture is used, exogenous trypsin or another protease can be added to the cell culture. Alternatively, exogenous trypsin or another protease can ectopically be expressed in the cells of the cell culture. The correct amount of trypsin or of another protease that needs to be added for efficient activation of infectious units and to avoid cytotoxic effects varies for each virus and cell line. Trypsin preparations may also have to be treated with 6-(1-tosylamido-2-phenyl) ethyl chloromethyl ketone (TPCK) that inhibits contaminating chymotrypsin. Chymotrypsin may hydrolyse myxovirus surface proteins but does not activate the infectious units [36].

The protease cleavage site may be a monobasic or polybasic cleavage site. Viruses of lower pathogenicity carry, for example, monobasic cleavage sites. Said cleavage sites are processed by trypsin-like proteases. Viruses of higher pathogenicity carry, for example, polybasic cleavage sites. Said cleavage sites are accessible to a greater diversity of proteases, including, in particular, subtilisin-like proteases. This property broadens tissue tropism and allows for systemic virus spread inducing greater damage to organs and tissues [37, 38].

The term "protease", as used herein, encompasses any protease which may be used to proteolytically process a virus for activation. The protease may be trypsin, a trypsin-like protease, subtilisin, or a subtilisin-like protease. The trypsin-like protease may be selected from the group consisting of trypsin, chymotrypsin, elastase, and plasmin. The subtilisin-like protease may be selected from the group consisting of subtilisin and furin. Serine proteases fall, based on their structure, into both categories of trypsin-like and subtilisin-like proteases.

The term "virus infectivity", as used herein, refers to the ability of a virus to replicate in a cell and to produce viral particles. The ability to measure the amount of infectious virus present in virus-containing cell is important and useful, particularly for determining the input multiplicity of infection (MOI). There are different methods known which all allow to determine the infectivity of a virus. Said methods may include, but are not limited to, plaque-based assays, focus forming assays (FFAs), measurements of the 50% Tissue culture Infective Dose ($TCID_{50}$), and hemagglutination assays (HAs).

In the context of the present patent application, the 50% Tissue culture Infective Dose ($TCID_{50}$) assay and the HA assay have been performed (see experimental part).

The term "environmental sample suspected of containing a virus", as used herein, refers to any small part of the environment which is of interest and which is suspected of containing a virus. The environmental sample may be a sample obtained from water, e.g. drinking water or sea water, particularly contaminated water, or earth. It may also be a clinical sample, e.g. a stool sample, an urine sample, or a blood sample. It may further be a sample obtained from an animal farm, e.g. pig or poultry farm. Additional environmental samples may include, but are not limited to, tracheal or bursal swaps, or biopsies from diseased animals or from sentry animals intentionally exposed to potential pathogens.

EMBODIMENTS OF THE INVENTION

Animal derived components, especially bovine serum, can be contaminated with adventitious agents that can cause disease in viral vaccine recipients and that complicate transboundary dissemination of viral vaccine preparations. For that reason, it is highly desirable that the cell line is capable of proliferating in medium free of animal-derived components. The inventors of the present patent application developed a novel and advantageous continuous porcine cell line that is capable of proliferating in medium free of animal-derived components. This cell line allows the production of viruses such as influenza viruses in high yields. Said viruses may be used as vaccines. It also relieves the selective pressures on the virus and, thus, interferes with accumulation of mutations in structural genes.

Thus, in a first aspect, the present invention relates to a continuous porcine cell line that is capable of proliferating in medium free of animal-derived components.

Preferably, the medium free of animal-derived components is a chemically-defined medium.

It is preferred that the cell line is a non-adherent cell line.

It is further preferred that the cell line is permissive for a virus. It is more preferred that the cell line is highly permissive for a virus. It is most preferred that the cell line is highly permissive and highly susceptible for a virus.

The virus may be a wild-type virus, a mutated virus, a cold-adapted virus, an attenuated virus, or a viral vector. The virus may also be a vaccine.

Thus, in a preferred embodiment, the continuous porcine cell line is a cell line that is capable of proliferating in medium free of animal-derived components and that is permissive for a virus. In a more preferred embodiment, the continuous porcine cell line is a non-adherent cell line that is capable of proliferating in medium free of animal-derived components and that is permissive for a virus.

The cell line described above may be
infected with a/the virus, or
transfected with a plasmid carrying (a) nucleic acid sequence(s) encoding a/the virus.
It should be noted that, depending on the virus used, the cell line may be transfected with one or more plasmids, e.g. 1, 2, 3, 4, 5, 6, 7, 8, 9, 10, 11, or 12 plasmids, carrying (a) nucleic acid sequence(s) encoding the virus. For example, the influenza A genome contains 11 genes on eight pieces of RNA, encoding for 11 proteins: hemagglutinin (HA), neuraminidase (NA), nucleoprotein (NP), M1, M2, NS1, NS2 (NEP: nuclear export protein), PA, PB1 (polymerase basic 1), PB1-F2 and PB2. Thus, the cell line may be transfected with 11 plasmids (one for each protein). It is also possible that one plasmid carries nucleic acid sequences encoding two or more proteins, e.g. 2, 3, or 4 proteins. The infection or transfection may be performed according to standard procedures known to the person skilled in the art.

As mentioned above, the cell line is permissive for a virus. The cell line may (further) be infected with a/the virus or transfected with a plasmid carrying (a) nucleic acid sequence(s) encoding a/the virus. Said virus may be
a negative-sense single stranded RNA ((−) ssRNA) virus,
a positive-sense single stranded RNA ((+) ssRNA) virus,
a double stranded RNA (dsRNA) virus,
a DNA-containing virus such as a double stranded DNA (dsDNA) virus or a single stranded DNA (ssDNA) virus,
a single stranded RNA retrovirus (ssRNA-RT virus), or
a double stranded DNA reverse transcriptase containing virus (dsDNA-RT virus).
Preferably,
the negative-sense single stranded RNA ((−) ssRNA) virus is a myxovirus, more preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double stranded RNA (dsRNA) virus is a virus of the Reoviridae family,
the DNA-containing virus is a virus of the Herpesviridae, Circoviridae, or Asfariviridae family,
the single stranded retrovirus (ssRNA-RT virus) is a virus of the Retroviridae family, or
the double stranded DNA reverse transcriptase containing virus (dsDNA-RT virus) is a virus of the Hepadnaviridae family.
More preferably,
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus,
the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

As mentioned above, the cell line is permissive for a virus. The cell line may (further) be infected with a/the virus or transfected with a plasmid carrying (a) nucleic acid sequence(s) encoding a/the virus. Said virus preferably carries a protease cleavage site. In particular, this cleavage site is required for activation of virus infectivity. More preferably, said virus carrying a protease cleavage site is
a negative-sense single stranded RNA ((−) ssRNA) virus,
a positive-sense single stranded RNA ((+) ssRNA) virus,
a double stranded RNA (dsRNA) virus, or
a DNA-containing virus.
Even more preferably,
the negative-sense single stranded RNA ((−) ssRNA) virus is a myxovirus, preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double stranded RNA (dsRNA) virus is a virus of the Reoviridae family, or
the DNA-containing virus is a virus of the Herpesviridae, Circoviridae, or Asfariviridae family. Most preferably,
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus, the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

Thus, in a more preferred embodiment, the continuous porcine cell line is a cell line that is capable of proliferating in medium free of animal-derived components and that is permissive for a virus carrying a protease cleavage site. The virus carrying a protease cleavage site is preferably a virus as described above. In an even more preferred embodiment, the continuous porcine cell line is a non-adherent cell line that is capable of proliferating in medium free of animal-derived components and that is permissive for a virus carrying a protease cleavage site. The virus carrying a protease cleavage site is preferably a virus as described above.

The protease cleavage site may be a monobasic or polybasic cleavage site. Viruses of lower pathogenicity carry, for example, monobasic cleavage sites. Said cleavage sites are processed by trypsin-like proteases. Viruses of higher pathogenicity carry, for example, polybasic cleavage sites. Said cleavage sites are accessible to a greater diversity of proteases, including, in particular, subtilisin-like proteases.

It is also, alternatively or additionally, preferred that the cell line does not require an exogenous protease for activation of virus infectivity. The exogenous protease may be trypsin, a trypsin-like protease, subtilisin, or a subtilisin-like protease. The trypsin-like protease may be selected from the group consisting of trypsin, chymotrypsin, elastase, and plasmin. The subtilisin-like protease may be selected from the group consisting of subtilisin and furin. Serine proteases fall, based on their structure, into both categories of trypsin-like and subtilisin-like proteases. In other words, it is also, alternatively or additionally, preferred that the cell line comprises an endogenous protease for activation of virus infectivity. Accordingly, virus production processes can be designed to be more robust and cost-effective because the addition of a exogenous protease such as trypsin to the cell culture is not necessary.

Thus, in a preferred embodiment, the continuous porcine cell line is a cell line that is capable of proliferating in medium free of animal-derived components and that does not require an exogenous protease for activation of virus infectivity or comprises an endogenous protease for activation of virus infectivity.

In a more preferred embodiment, the continuous porcine cell line is a cell line that is capable of proliferating in medium free of animal-derived components, that is permissive for a virus and that does not require an exogenous protease for activation of virus infectivity or comprises an endogenous protease for activation of virus infectivity. The virus is preferably a virus as described above.

In an even more preferred embodiment, the continuous porcine cell line is a cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

In a most preferred embodiment, the continuous porcine cell line is a non-adherent cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

Preferably, the continuous porcine cell line is a kidney cell line or a testis cell line. In this respect, the following embodiments are preferred:

(a) The continuous porcine kidney or testis cell line is a cell line that is capable of proliferating in medium free of animal-derived components and that is permissive for a virus.

(b) The continuous porcine kidney or testis cell line is a non-adherent cell line that is capable of proliferating in medium free of animal-derived components and that is permissive for a virus.

(c) The continuous porcine kidney or testis cell line is a cell line that is capable of proliferating in medium free of animal-derived components and that is permissive for a virus carrying a protease cleavage site. The virus carrying a protease cleavage site is preferably a virus as described above.

(d) The continuous porcine kidney or testis cell line is a non-adherent cell line that is capable of proliferating in medium free of animal-derived components and that is permissive for a virus carrying a protease cleavage site. The virus carrying a protease cleavage site is preferably a virus as described above.

(e) The continuous porcine kidney or testis cell line is a cell line that is capable of proliferating in medium free of animal-derived components and that does not require an exogenous protease for activation of virus infectivity or comprises an endogenous protease for activation of virus infectivity.

(f) The continuous porcine kidney or testis cell line is a cell line that is capable of proliferating in medium free of animal-derived components, that is permissive for a virus and that does not require an exogenous protease for activation of virus infectivity or comprises an endogenous protease for activation of virus infectivity. The virus is preferably a virus as described above.

(g) The continuous porcine kidney or testis cell line is a cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

(h) The continuous porcine kidney or testis cell line is a non-adherent cell line that is capable of proliferating in medium free of animal-derived components, that is permissive for a virus carrying a protease cleavage site and that does not require an exogenous protease for activation of virus infectivity or comprises an endogenous protease for activation of virus infectivity.

The virus carrying a protease cleavage site is preferably a virus as described above.

In a particularly preferred embodiment, the cell line is PK-15S. The "S" at the end of the cell line name "PK-15S" stands for the ability of this cell line to proliferate in medium free of animal-derived components, preferably in chemically defined medium. The cell line PK-15S is further a continuous and non-adherent cell line. The cell line PK-15S is derived from PK-15. PK-15 is a cell line of adherently proliferating pig kidney cells. Said cell line has preferentially been used to isolate the classical swine fever virus [39] and (with appropriate genetic modification) the porcine reproductive and respiratory syndrome virus (PRRSV) [40].

The cell line PK-15S is a cell line deposited at the DSMZ with the deposit number DSM ACC3307. In particular, the cell line PK-15S was deposited with the DSMZ-Deutsche Sammlung von Mikroorganismen and Zellkulturen GmbH, Inhoffenstrasse 7B, 38124 Braunschweig, Germany on Sep. 21, 2016 under accession number DSM ACC3307.

Preferably, the PK-15S cell line is a cell line that is permissive for a virus. Said virus is preferably a virus as described above.

More preferably, the PK-15S cell line is a cell line that is permissive for a virus carrying a protease cleavage site. Said virus carrying a protease cleavage site is preferably a virus as described above. Alternatively, the PK-15S cell line is a cell line that does not require an exogenous protease for activation of virus infectivity or comprises an endogenous protease for activation of virus infectivity. Even more preferably, the PK-15S cell line is a cell line that is permissive for a virus and that does not require an exogenous protease for activation of virus infectivity or comprises an endogenous protease for activation of virus infectivity. The virus is preferably a virus as described above.

Most preferably, the PK-15S cell line is a cell line that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

For example, the PK-15S cell line is highly permissive and/or highly susceptible for influenza A virus, preferably low pathogenic influenza A virus. In addition, the PK-15S cell line is highly permissive and/or highly susceptible for Newcastle disease virus (NDV), preferably lentogenic Newcastle disease virus (NDV).

In another particularly preferred embodiment, the cell line is STS. The "S" at the end of the cell line name "STS" stands for the ability of this cell line to proliferate in medium free of animal-derived components. The cell line STS is further a continuous and non-adherent cell line. The cell line STS is derived from ST. ST is a cell line obtained from testicular Sertoli cells of *Sus scrofa*. This cell line is reported to proliferate only in adherent culture formats [41]. Preferably, the cell line STS is a cell line deposited at the DSMZ with the deposit number DSM ACC3308. In particular, the cell line STS was deposited with the DSMZ-Deutsche Sammlung von Mikroorganismen and Zellkulturen GmbH, Inhoffenstrasse 7B, 38124 Braunschweig, Germany on Sep. 21, 2016 under accession number DSM ACC3308.

Preferably, the STS cell line is a cell line that is permissive for a virus. Said virus is preferably a virus as described above.

More preferably, the STS cell line is a cell line that is permissive for a virus carrying a protease cleavage site. Said virus carrying a protease cleavage site is preferably a virus as described above. Alternatively, the STS cell line is a cell line that does not require an exogenous protease for activation of virus infectivity or comprises an endogenous protease for activation of virus infectivity.

Even more preferably, the STS cell line is a cell line that is permissive for a virus and that does not require an exogenous protease for activation of virus infectivity or comprises an endogenous protease for activation of virus infectivity. The virus is preferably a virus as described above.

Most preferably, the STS cell line is a cell line that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

For example, the STS cell line is highly permissive and/or highly susceptible for influenza A virus, preferably low pathogenic influenza A virus. In addition, the STS cell line is highly permissive and/or highly susceptible for Newcastle disease virus (NDV), preferably lentogenic Newcastle disease virus (NDV).

Others have tested infection with influenza viruses in PK-15 cell lines and report low titers [42] or no replication at all [43]. There also appears to be a high and interfering interferon sensitivity in PK-15 after infection with influenza viruses [44]. The inventors of the present patent application were, therefore, very surprised that the infection of the PK-15S and STS cell lines with influenza virus resulted in a strong influenza virus production. The described system is also independent of exogenous trypsin addition. Reason for this is that the PK-15S and STS cell lines comprise an endogenous protease for activation of virus infectivity.

It is particularly preferred that the cell line is not contaminated with material from other cell cultures. The material from other cell cultures may comprise simian cells, canine cells, or other porcine cells. This ensures that the quality and integrity of the cell line is maintained.

Preferably, the cell line proliferates for at least 10 passages, at least 20 passages, or at least 30 passages in medium free of animal-derived components such as chemically-defined medium, prior to inoculation of a bioreactor for virus production, particularly vaccine production.

The inventors of the present patent application surprisingly found that the novel and advantageous continuous porcine cell line of the present invention allows the production of viruses in high yields. Said produced viruses may be used as vaccines.

Thus, in a second aspect, the present invention relates to a method for producing a virus comprising the steps of:
(i) providing a continuous porcine cell line that is capable of proliferating in medium free of animal-derived components, preferably in chemically defined medium, and that is permissive for the virus,
(ii) infecting said cell line with the virus or transfecting said cell line with a plasmid carrying (a) nucleic acid sequence(s) encoding the virus, and
(iii) culturing the cell line infected or transfected in step (ii), thereby producing the virus.

Step (i) of the above method requires that a continuous porcine cell line that is capable of proliferating in medium free of animal-derived components, preferably in chemically defined medium, and that is permissive for the virus is provided.

It is preferred that the cell line (provided in step (i)) is a non-adherent cell line.

It is further, alternatively or additionally, preferred that the cell line (provided in step (i)) is highly permissive for the virus. It is more preferred that the cell line (provided in step (i)) is permissive and susceptible for the virus. It is even more preferred that the cell line (provided in step (i)) is highly permissive and highly susceptible for the virus.

The virus may be a wild-type virus, a mutated virus, a live virus, an inactivated virus, a cold-adapted virus, an attenuated virus (e.g. a highly attenuated virus), or a viral vector. The virus may also be a vaccine.

Thus, in a preferred embodiment, the continuous porcine cell line (provided in step (i)) is a non-adherent cell line that is capable of proliferating in medium free of animal-derived components and that is permissive for the virus.

The virus produced with the above method/the virus for which the cell line (provided in step (i)) is permissive may be
a negative-sense single stranded RNA ((−) ssRNA) virus,
a positive-sense single stranded RNA ((+) ssRNA) virus,
a double stranded RNA (dsRNA) virus,
a DNA-containing virus such as a double stranded DNA (dsDNA) virus or a single stranded DNA (ssDNA) virus,
a single stranded RNA retrovirus (ssRNA-RT virus), or
a double stranded DNA reverse transcriptase containing virus (dsDNA-RT virus).
Preferably,
the negative-sense single stranded RNA ((−) ssRNA) virus is a myxovirus, more preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double stranded RNA (dsRNA) virus is a virus of the Reoviridae family,
the DNA-containing virus is a virus of the Herpesviridae, Circoviridae, or Asfariviridae family,
the single stranded retrovirus (ssRNA-RT virus) is a virus of the Retroviridae family, or
the double stranded DNA reverse transcriptase containing virus (dsDNA-RT virus) is a virus of the Hepadnaviridae family.
More preferably,
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus,
the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

Said virus preferably carries a protease cleavage site. In particular, this cleavage site is required for activation of virus infectivity. More preferably, said virus carrying a protease cleavage site is
a negative-sense single stranded RNA ((−) ssRNA) virus,
a positive-sense single stranded RNA ((+) ssRNA) virus,
a double-stranded RNA (dsRNA) virus, or
a DNA-containing virus.

Even more preferably, the negative-sense single stranded RNA ((−) ssRNA) virus is a myxovirus, preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double-stranded RNA (dsRNA) virus is a virus of the Reoviridae family, or
the DNA-containing virus is a virus of the Herpesviridae, Circoviridae, or Asfariviridae family.

Most preferably, the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus,
the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

Thus, in another preferred embodiment, the continuous porcine cell line (provided in step (i)) is a cell line that is capable of proliferating in medium free of animal-derived components and that is permissive for the virus carrying a protease cleavage site. The virus carrying a protease cleavage site is preferably a virus as described above.

In a more preferred embodiment, the continuous porcine cell line (provided in step (i)) is a non-adherent cell line that is capable of proliferating in medium free of animal-derived components and that is permissive for the virus carrying a protease cleavage site. The virus carrying a protease cleavage site is preferably a virus as described above.

The protease cleavage site may be a monobasic or polybasic cleavage site. Viruses of lower pathogenicity carry, for example, monobasic cleavage sites. Said cleavage sites are processed by trypsin-like proteases. Viruses of higher pathogenicity carry, for example, polybasic cleavage sites. Said cleavage sites are accessible to a greater diversity of proteases, including, in particular, subtilisin-like proteases.

It is also, alternatively or additionally, preferred that the cell line (provided in step (i)) does not require an exogenous protease for activation of virus infectivity. The exogenous protease may be trypsin, a trypsin-like protease, subtilisin, or a subtilisin-like protease. The trypsin-like protease may be selected from the group consisting of trypsin, chymotrypsin, elastase, and plasmin. The subtilisin-like protease may be selected from the group consisting of subtilisin and furin. Serine proteases fall, based on their structure, into both categories of trypsin-like and subtilisin-like proteases. In other words, it is also, alternatively or additionally, preferred that the cell line (provided in step (i)) comprises an endogenous protease for activation of virus infectivity.

Thus, in another preferred embodiment, the continuous porcine cell line (provided in step (i)) is a cell line that is capable of proliferating in medium free of animal-derived components, that is permissive for the virus and that does not require an exogenous protease for activation of virus infectivity or comprises an endogenous protease for activation of virus infectivity. The virus is preferably a virus as described above.

In a more preferred embodiment, the continuous porcine cell line (provided in step (i)) is a cell line that is capable of proliferating in medium free of animal-derived components, that is permissive for the virus carrying a protease cleavage site and that does not require an exogenous protease for activation of virus infectivity or comprises an endogenous protease for activation of virus infectivity. The virus carrying a protease cleavage site is preferably a virus as described above.

In an even more preferred embodiment, the continuous porcine cell line (provided in step (i)) is a non-adherent cell line that is capable of proliferating in medium free of animal-derived components, that is permissive for the virus carrying a protease cleavage site and that does not require an exogenous protease for activation of virus infectivity or comprises an endogenous protease for activation of virus infectivity. The virus carrying a protease cleavage site is preferably a virus as described above.

Preferably, the porcine cell line is a kidney cell line or a testis cell line. In this respect, the following embodiments are preferred:
(a) The continuous porcine kidney or testis cell line (provided in step (i)) is a non-adherent cell line that is capable of proliferating in medium free of animal-derived components and that is permissive for the virus.
(b) The continuous porcine kidney or testis cell line (provided in step (i)) is a cell line that is capable of proliferating in medium free of animal-derived components and that is permissive for the virus carrying a protease cleavage site. The virus carrying a protease cleavage site is preferably a virus as described above.
(c) The continuous porcine kidney or testis cell line (provided in step (i)) is a non-adherent cell line that is capable of proliferating in medium free of animal-derived components and that is permissive for the virus carrying a protease cleavage site. The virus carrying a protease cleavage site is preferably a virus as described above.
(d) The continuous porcine kidney or testis cell line (provided in step (i)) is a cell line that is capable of proliferating in medium free of animal-derived components, that is permissive for the virus and that does not require an exogenous protease for activation of virus infectivity or comprises an endogenous protease for activation of virus infectivity. The virus is preferably a virus as described above.
(e) The continuous porcine kidney or testis cell line (provided in step (i)) is a cell line that is capable of proliferating in medium free of animal-derived components, that is permissive for the virus carrying a protease cleavage site and that does not require an exogenous protease for activation of virus infectivity or comprises an endogenous protease for activation of virus infectivity. The virus carrying a protease cleavage site is preferably a virus as described above.
(f) The continuous porcine kidney or testis cell line (provided in step (i)) is a non-adherent cell line that is capable of proliferating in medium free of animal-derived components, that is permissive for the virus carrying a protease cleavage site and that does not require an exogenous protease for activation of virus infectivity or comprises an endogenous protease for activation of virus infectivity. The virus carrying a protease cleavage site is preferably a virus as described above.

In a particularly preferred embodiment, the cell line (provided in step (i)) is PK-15S. The cell line PK-15S is derived from PK-15. It is deposited at the DSMZ with the deposit number DSM ACC3307. The cell line PK-15S is a continuous and non-adherent cell line that is capable of proliferating in medium free of animal-derived components, preferably in chemically defined medium. The PK-15S cell line is further a cell line that is permissive for the virus. Said virus is preferably a virus as described above.

Preferably, the PK-15S cell line is a cell line that is permissive for the virus carrying a protease cleavage site. Said virus carrying a protease cleavage site is preferably a virus as described above. More preferably, the PK-15S cell line is a cell line that is permissive for the virus and that does not require an exogenous protease for activation of virus infectivity or comprises an endogenous protease for activation of virus infectivity. The virus is preferably a virus as described above.

Even more preferably, the PK-15S cell line is a cell line that is permissive for the virus carrying a protease cleavage site and that does not require an exogenous protease for activation of virus infectivity or comprises an endogenous protease for activation of virus infectivity. The virus carrying a protease cleavage site is preferably a virus as described above.

For example, the PK-15S cell line is highly permissive and/or highly susceptible for influenza A virus, preferably low pathogenic influenza A virus. In addition, the PK-15S cell line is highly permissive and/or highly susceptible for Newcastle disease virus (NDV), preferably lentogenic Newcastle disease virus (NDV).

In another particularly preferred embodiment, the cell line (provided in step (i)) is STS. The cell line STS is derived from ST. It is deposited at the DSMZ with the deposit number DSM ACC3308. The cell line STS is a continuous and non-adherent cell line that is capable of proliferating in medium free of animal-derived components. The STS cell line is further a cell line that is permissive for the virus. Said virus is preferably a virus as described above.

Preferably, the STS cell line is a cell line that is permissive for the virus carrying a protease cleavage site. Said virus is preferably a virus as described above.

More preferably, the STS cell line is a cell line that is permissive for the virus and that does not require an exogenous protease for activation of virus infectivity or comprises an endogenous protease for activation of virus infectivity. The virus is preferably a virus as described above.

Even more preferably, the STS cell line is a cell line that is permissive for the virus carrying a protease cleavage site and that does not require an exogenous protease for activation of virus infectivity or comprises an endogenous protease for activation of virus infectivity. The virus is preferably a virus as described above.

For example, the STS cell line is highly permissive and/or highly susceptible for influenza A virus, preferably low pathogenic influenza A virus. In addition, the STS cell line is highly permissive and/or highly susceptible for Newcastle disease virus (NDV), preferably lentogenic Newcastle disease virus (NDV).

It is particularly preferred that the cell line (provided in step (i)) is not contaminated with material from other cell cultures. The material from other cell cultures may comprise simian cells, canine cells, or other porcine cells. This ensures that the quality and integrity of the cell line is maintained.

Step (ii) of the above method requires that said cell line is infected with the virus or transfected with a plasmid carrying (a) nucleic acid sequence(s) encoding the virus.

Regarding step (ii), it should be noted that, depending on the virus used, the cell line may be transfected with one or more plasmids, e.g. 1, 2, 3, 4, 5, 6, 7, 8, 9, 10, 11, or 12 plasmids, carrying (a) nucleic acid sequence(s) encoding the virus. For example, the influenza A genome contains 11 genes on eight pieces of RNA, encoding for 11 proteins: hemagglutinin (HA), neuraminidase (NA), nucleoprotein (NP), M1, M2, NS1, NS2 (NEP: nuclear export protein), PA, PB1 (polymerase basic 1), PB1-F2 and PB2. Thus, the cell line may be transfected with 11 plasmids (one for each protein). It is also possible that one plasmid carries nucleic acid sequences encoding two or more proteins, e.g. 2, 3, or 4 proteins.

The infection or transfection may be performed according to standard procedures known to the person skilled in the art.

Preferably, the virus in step (ii) has a MOI in the range of $10^{-7}$ and 1. In particular, the virus is an Influenza A virus or a Newcastle disease virus.

Step (iii) of the above method requires that the cell line infected or transfected in step (ii) is cultured. Thereby, the virus is produced.

Culturing in step (iii) may be performed according to standard procedures readily available to the skilled person. In this respect, is should be noted that culture/incubation times are important for the production of viruses in high yields. A sufficiently long incubation time allows virus to spread from the initially few infected cells throughout the culture. Once all possible cells are infected, further incubation times may decrease yields as viruses may become degraded. In addition, since virus replication depends on the cells energetic and metabolic capacity, it is desirable to keep cell viability at a high level over the duration of upstream processing.

The culturing time may range between 1 day and 24 days, more preferably between 3 and 24 days, most preferably between 5 and 24 days, e.g. 1, 2, 3, 4, 5, 6, 7, 8, 9, 10, 11, 12, 13, 14, 15, 16, 17, 18, 19, 20, 21, 22, 23, or 24 days. The cell line may be cultured in step (iii) in an agitated culture in shaken culture flasks or culture bags or in a bioreactor.

It is further, alternatively or additionally, preferred that the method further comprises step (iv) of isolating the virus cultured in step (iii).

Various virus isolation procedures are known in the art. An isolation procedure which is useful according to the invention does not interfere with the virus to be isolated. For example, extended exposure to impeller shear forces and other factors that occur during harvesting should be avoided. It is preferred that isolation in step (iv) is achieved by separating the virus from said cell via centrifugation, sedimentation and/or filtration, e.g. via centrifugation and filtration, via sedimentation and filtration, via sedimentation and centrifugation, or via centrifugation, sedimentation and filtration. Depending on the virus to be isolated, the parameters for centrifugation, sedimentation or filtration may vary. The person skilled in the art is able to easily adapt the appropriate separation parameters, e.g. the acceleration-force/G-force and/or time using centrifugation for separation, filter size using filtration for separation, and/or sedimentation time using sedimentation for separation, in order to isolate the virus produced by said cells.

Preferably, the cell line proliferates for at least 10 passages, at least 20 passages, or at least 30 passages in medium free of animal derived components such as chemically-defined medium prior to inoculation of a bioreactor for virus production, particularly vaccine production.

It is particularly preferred that the virus used for infection (virus seed) and the virus produced do not differ in their properties relevant for vaccine efficacy.

The virus produced with the above method may be a vaccine. Said viral vaccine may be used for vaccination, e.g. of humans or animals.

In a third aspect, the present invention relates to a virus obtainable by the method according to the second aspect.

The virus may be used for vaccination. The virus may further be comprised in a composition, e.g. in a pharmaceutical composition. Said pharmaceutical composition may be a composition used for vaccination.

The inventors of the present patent application surprisingly found that the novel and advantageous continuous porcine cell line of the present invention allows the accumulation of viruses found in environmental samples. Said accumulated viruses may be used as seeds in virus production processes.

Thus, in a fourth aspect, the present invention relates to a method for accumulating a virus from an environmental sample comprising the steps of:
(i) providing a continuous porcine cell line that is capable of proliferating in medium free of animal-derived components, preferably in chemically defined medium, and that is permissive for a virus,
(ii) contacting said cell line with an environmental sample suspected of containing a virus,
(iii) culturing the cell line contacted in step (ii), thereby accumulating the virus.

Step (i) of the above method requires that a continuous porcine cell line that is capable of proliferating in medium free of animal-derived components, preferably in chemically defined medium, and that is permissive for a virus is provided.

It is preferred that the cell line (provided in step (i)) is a non-adherent cell line.

It is further, alternatively or additionally, preferred that the cell line (provided in step (i)) is highly permissive for a virus. It is more preferred that the cell line (provided in step (i)) is permissive and susceptible for a virus. It is even more preferred that the cell line (provided in step (i)) is highly permissive and highly susceptible for a virus.

Thus, in a preferred embodiment, the continuous porcine cell line (provided in step (i)) is a non-adherent cell line that is capable of proliferating in medium free of animal-derived components and that is permissive for a virus.

The virus accumulated with the above method/the virus for which the cell line (provided in step (i)) is permissive/the virus suspected to be contained in the environmental sample (of step (ii)) may be
a negative-sense single stranded RNA ((−) ssRNA) virus,
a positive-sense single stranded RNA ((+) ssRNA) virus,
a double stranded RNA (dsRNA) virus,
a DNA-containing virus such as a double stranded DNA (dsDNA) virus or a single stranded DNA (ssDNA) virus,
a single stranded RNA retrovirus (ssRNA-RT virus), or
a double stranded DNA reverse transcriptase containing virus (dsDNA-RT virus).
Preferably,
the negative-sense single stranded RNA ((−) ssRNA) virus is a myxovirus, more preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double stranded RNA (dsRNA) virus is a virus of the Reoviridae family,
the DNA-containing virus is a virus of the Herpesviridae, Circoviridae, or Asfariviridae family,
the single stranded retrovirus (ssRNA-RT virus) is a virus of the Retroviridae family, or
the double stranded DNA reverse transcriptase containing virus (dsDNA-RT virus) is a virus of the Hepadnaviridae family.

More preferably,
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus,
the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

Said virus preferably carries a protease cleavage site. In particular, this cleavage site is required for activation of virus infectivity. More preferably, said virus carrying a protease cleavage site is
a negative-sense single stranded RNA ((−) ssRNA) virus,
a positive-sense single stranded RNA ((+) ssRNA) virus,
a double stranded RNA (dsRNA) virus, or
a DNA-containing virus.
Even more preferably,
the negative-sense single stranded RNA ((−) ssRNA) virus is a myxovirus, preferably a virus of the Orthomyxoviridae or Paramyxoviridae family,
the positive-sense single stranded RNA ((+) ssRNA) virus is a virus of the Flaviviridae, Coronaviridae, or Arteriviridae family,
the double stranded RNA (dsRNA) virus is a virus of the Reoviridae family, or
the DNA-containing virus is a virus of the Herpesviridae, Circoviridae, or Asfariviridae family.
Most preferably,
the virus of the Orthomyxoviridae family is selected from the group consisting of influenza A virus, influenza B virus, influenza C virus, Isavirus, Quaranjavirus, and Thogotovirus,
the virus of the Paramyxoviridae family is selected from the group consisting of Newcastle disease virus, Sendai virus, measles virus, Hendra virus, and Nipah virus,
the virus of the Flaviviridae family is selected from the group consisting of Flavivirus, Pegivirus, and Pestivirus,
the virus of the Coronaviridae family is a porcine epidemic diarrhea virus (PEDV),
the virus of the Arteriviridae family is a porcine reproductive and respiratory syndrome virus (PRRSV),
the virus of the Reoviridae family is a seadornavirus selected from the group consisting of Banna virus (BAV), Kadipiro virus, and Liao ning virus,
the virus of the Herpesviridae family is a suid herpesvirus 1 (SuHV1),
the virus of the Circoviridae family is a porcine circovirus 1 or 2 (PCV-1 or PCV-2), or
the virus of the Asfariviridae family is African swine fever virus (ASFV).

Thus, in another preferred embodiment, the continuous porcine cell line (provided in step (i)) is a cell line that is capable of proliferating in medium free of animal-derived components and that is permissive for a virus carrying a protease cleavage site. The virus carrying a protease cleavage site is preferably a virus as described above.

In a more preferred embodiment, the continuous porcine cell line (provided in step (i)) is a non-adherent cell line that is capable of proliferating in medium free of animal-derived components and that is permissive for a virus carrying a protease cleavage site. The virus carrying a protease cleavage site is preferably a virus as described above.

The protease cleavage site may be a monobasic or polybasic cleavage site (see first and second aspect of the present invention).

It is also, alternatively or additionally, preferred that the cell line (provided in step (i)) does not require an exogenous protease for activation of virus infectivity. The exogenous protease may be trypsin, a trypsin-like protease, subtilisin, or a subtilisin-like protease. The trypsin-like protease may be selected from the group consisting of trypsin, chymotrypsin, elastase and plasmin. The subtilisin-like protease may be selected from the group consisting of subtilisin and furin. Serine proteases fall, based on their structure, into both categories of trypsin-like and subtilisin-like proteases. In other words, it is also, alternatively or additionally, preferred that the cell line (provided in step (i)) comprises an endogenous protease for activation of virus infectivity.

Thus, in another preferred embodiment, the continuous porcine cell line (provided in step (i)) is a cell line that is capable of proliferating in medium free of animal-derived components, that is permissive for a virus and that does not require an exogenous protease for activation of virus infectivity or comprises an endogenous protease for activation of virus infectivity. The virus is preferably a virus as described above.

In a more preferred embodiment, the continuous porcine cell line (provided in step (i)) is a cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

In an even more preferred embodiment, the continuous porcine cell line (provided in step (i)) is a non-adherent cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

Preferably, the porcine cell line is a kidney cell line or a testis cell line. In this respect, the following embodiments are preferred:
(a) The continuous porcine kidney or testis cell line (provided in step (i)) is a non-adherent cell line that is capable of proliferating in medium free of animal-derived components and that is permissive for a virus.
(b) The continuous porcine kidney or testis cell line (provided in step (i)) is a cell line that is capable of proliferating in medium free of animal-derived components and that is permissive for a virus carrying a protease cleavage site. The virus carrying a protease cleavage site is preferably a virus as described above.
(c) The continuous porcine kidney or testis cell line (provided in step (i)) is a non-adherent cell line that is capable of proliferating in medium free of animal-derived components and that is permissive for a virus carrying a protease cleavage site. The virus carrying a protease cleavage site is preferably a virus as described above.

(d) The continuous porcine kidney or testis cell line (provided in step (i)) is a cell line that is capable of proliferating in medium free of animal-derived components, that is permissive for a virus and that does not require an exogenous protease for activation of virus infectivity or comprises an endogenous protease for activation of virus infectivity. The virus is preferably a virus as described above.

(e) The continuous porcine kidney or testis cell line (provided in step (i)) is a cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

(f) The continuous porcine kidney or testis cell line (provided in step (i)) is a non-adherent cell line that is capable of proliferating in medium free of animal-derived components, that is permissive for a virus carrying a protease cleavage site and that does not require an exogenous protease for activation of virus infectivity or comprises an endogenous protease for activation of virus infectivity. The virus carrying a protease cleavage site is preferably a virus as described above.

In a particularly preferred embodiment, the cell line (provided in step (i)) is PK-15S. In this respect, it is referred to the first and second aspect of the present invention.

In another particularly preferred embodiment, the cell line (provided in step (i)) is STS. In this respect, it is referred to the first and second aspect of the present invention.

Step (ii) of the above method requires that the cell line is contacted with an environmental sample suspected of containing a virus. The contacting may take place by dropping the environmental sample to the cell line, in particular to the medium comprising the cell line. The contacting may also take place by mixing the environmental sample with the cell line, in particular the environmental sample with the medium comprising the cell line.

Step (iii) of the above method requires that the cell line contacted in step (ii) is cultured. Thereby, the virus is accumulated. Various culture techniques are known in the art. In this respect, it is referred to the second aspect of the present invention.

It is further, alternatively or additionally, preferred that the method further comprises step (iv) of isolating the virus cultured in step (iii). Various virus isolation procedures are known in the art. In this respect, it is referred to the second aspect of the present invention.

The virus accumulated with the above method may be used as a seed in the virus production process.

In a fifth aspect, the present invention relates to a virus obtainable by the method according to the fourth aspect. The virus may be used as a seed in the virus production process. The virus may also be used for vaccination. The virus may further be comprised in a composition, e.g. in a pharmaceutical composition. The pharmaceutical composition may be a composition used for vaccination.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures and examples are merely illustrative of the present invention and should not be construed to limit the scope of the invention as indicated by the appended claims in any way.

Figure 6:
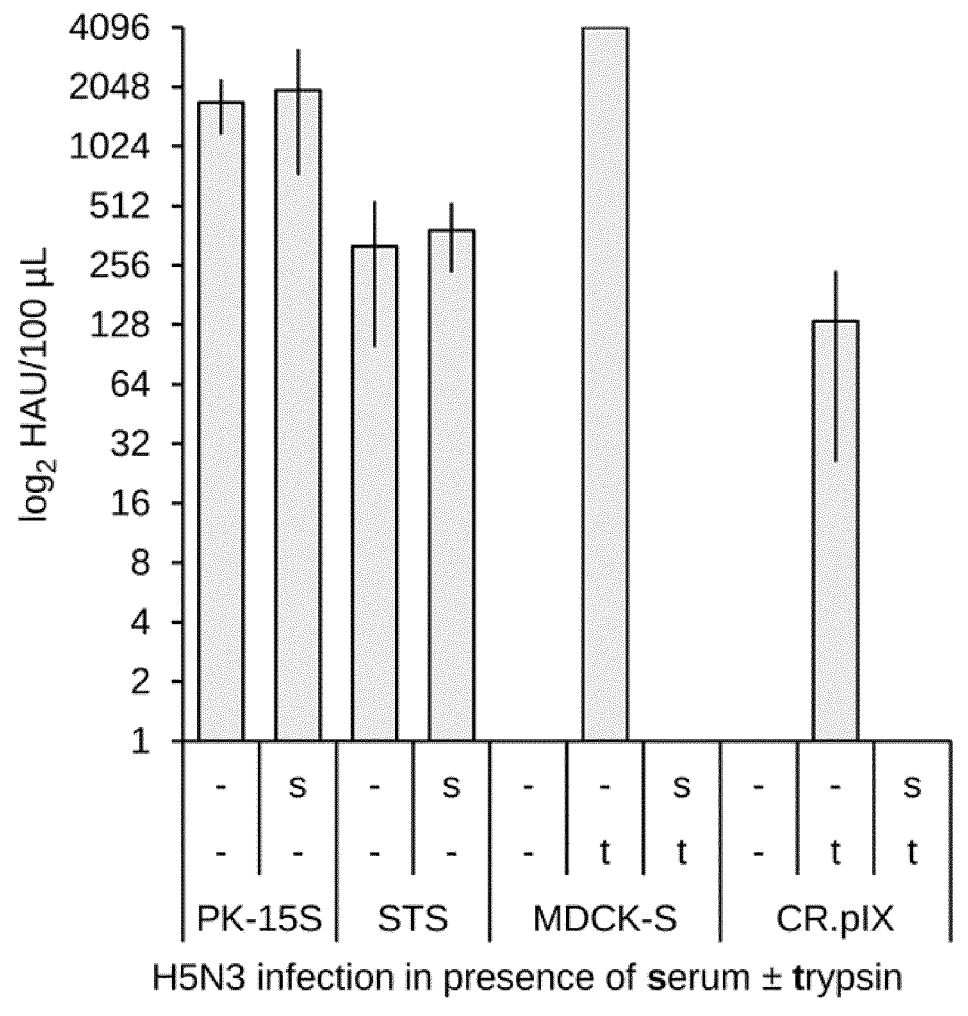

FIG. 6: PK-15S and STS allows influenza virus propagation without exogenous protease addition. Replication of para- and orthomyxoviruses is inhibited in CR.pIX and MDCK cultures without addition of trypsin. (−) for no supplementation, (s) for addition of bovine serum to 2%, (t) for 16 U/mL trypsin per day. Shown are mean and standard deviation of at least 4 independent experiments. The chart depicts values obtained 3 days post infection.

EXAMPLES

The examples given below are for illustrative purposes only and do not limit the invention described above in any way.

1.1 Stable Adaption to Single-Cell Suspension Cultivation

Adaptation of adherent cells to proliferation in suspension and without dependence on serum is complex and unique for each cell line [46,47]. However, this step is important to obtain a system suitable for veterinary vaccine production that requires efficient, robust and highly cost-effective solutions. The significant advantages of single-cell suspension production systems suitable for cultivation in scalable bioreactors is briefly discussed in the context of peste des petits ruminants (PPR) vaccines [48], but the same considerations apply for all veterinary and human vaccines, especially if they are required at higher volumes and doses. The burden associated with bovine serum are discussed in the context of introduction of adventitious agents to pharmaceutical products [46].

Successful adaptation to proliferation without serum and to proliferation in suspension induces profound changes in cell cultures. The affected cell lines must be guided through modulations in metabolic pathways, apoptotic cascades, cytoskeleton integrity, and intracellular vesicle targeting.

Metabolic pathways shift because the wide spectrum of growth factors cannot be provided by chemically-defined medium or plant hydrolysates. Apoptosis needs to remain suppressed also in the absence of protective serum factors, and receptors responsible for anoikis induction must ignore absence of adhesion signals that are normally provided by the growth support and neighbouring cells. The cytoskeleton, a pervasive structure throughout the cell, must rearrange with the transition from anchored fusiforms to the artificially induced spheres. Finally, transport of cellular (and viral) components along actin filaments and microtubule tracks must be reorganized as cell polarity is lost in a suspension cell without basal and apical surfaces. The results are observable extensive and global shifts in the genome and proteome [49] so that parental cell and derived progeny are highly divergent and not interchangeable anymore. To avoid ambiguities due to this development, the cell lines that have shifted signalling and metabolic pathways towards a novel generation are denoted with the suffix S→G+(PK-15S→G+, STS→G+, or abbreviated PK-15S and STS).

The process towards adaptation was characterized by phases with very low proliferation rates and viabilities that had to be alternated with subtle changes to the media and culture formats to prevent loss of the cultures.

Figure 1:
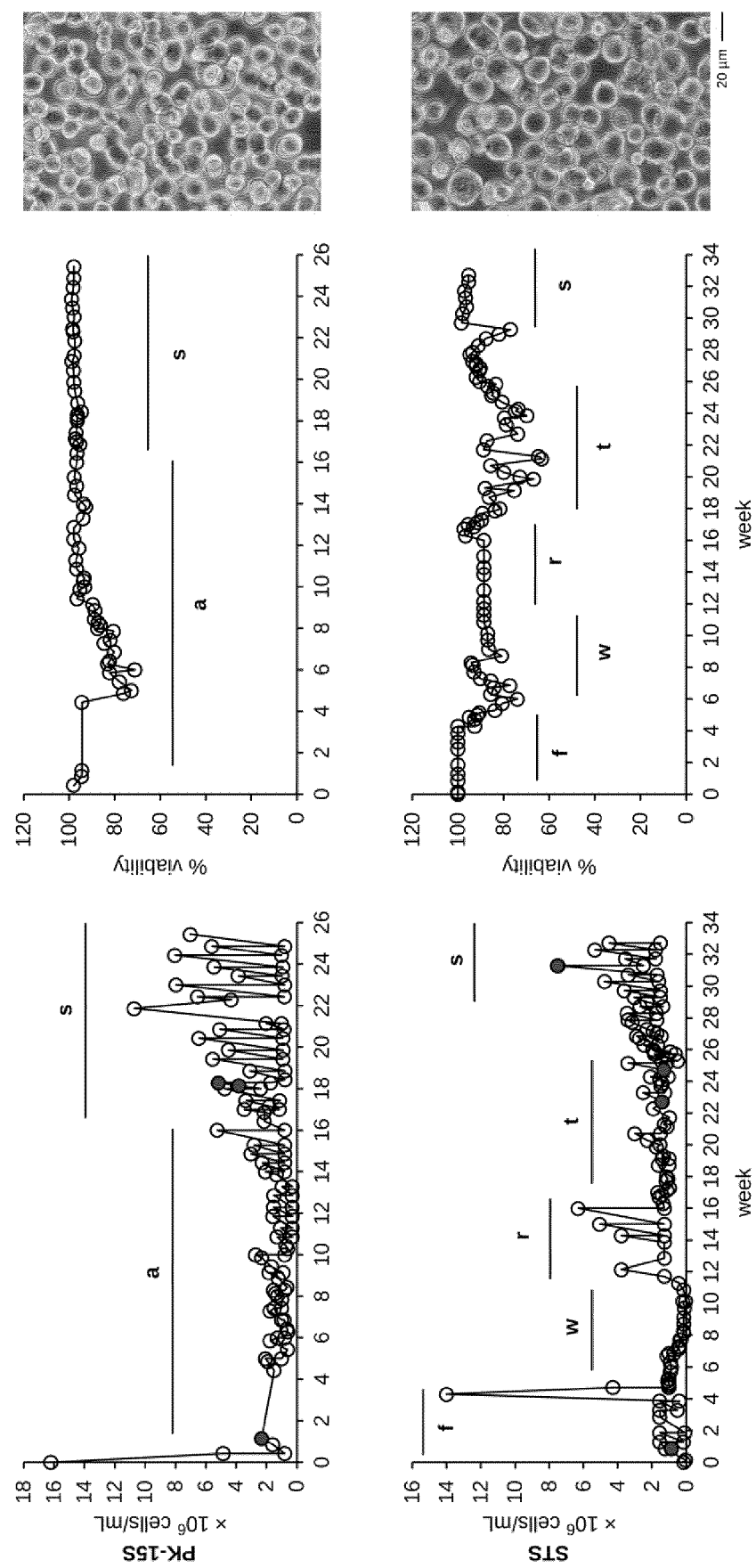
FIG. 1: PK-15S and STS passage diagrams depicting cell densities (left) and viabilities (right). Generation of cell populations suitable for propagation in medium free of animal-derived components. Both cultures required an adaptation phase of at least 16 weeks. Especially generation of STS was complex and required shifts between semi-adherent and suspension culture formats. The semi-adherent culture format was achieved by supplementation of the CD-U4 medium with 0.1 volumes of DMEM. The letters in the chart denote: a, adaptation to animal-derived component free medium; r, rescue of adapted cell population; s, subcultivation and stabilization of final cell population; t, shift in culture format from semi-adherent to single-cell suspension; w, withdrawal of fetal calf serum; f, fetal calf serum. The right panel shows cell morphologies and size distribution of the final suspension cell lines.

The experimental steps were the following: The adherent PK-15 cells were trypsinized and re-suspended to approx. 15×10$^6$ cells/mL in a cell culture medium based on CD-U4. CD-U4 cell culture medium is a modification of DMEM and can be obtained, for example, from GE Healthcare under catalogue T1313. Viability and cell density immediately decreased significantly (see FIG. 1). The cells were next adapted by continuous cultivation after dispersal of cell aggregates using cell-strainers and plant-derived trypsin during week 0 to 6. Suitable cell populations were rescued stepwise, by variation of medium composition during a passage, to a chemically-defined CD-U4-derivative over the course of further 10 weeks. Variations of the culture medium included supplementation with insulin-like growth factor between 10 and 150 ng/mL; glucose between 5 and 8 g/L; glutamine between 1 and 4 mM; bovine serum in a declining sequence from 1% to 0% in steps of 0.2%; CaCl$_2$) from 21 to 27 mg/L; Fe(NO$_3$)$_3$*9H$_2$O from 0.008 to 0.010 mg/L; MgSO4 from 7.8 to 9.9 mg/L; KCl from 32 to 41 mg/L; NaHCO$_3$ from 296 to 376 mg/L; NaCl from 512 to 650 mg/L; NaH$_2$PO$_4$ from 8.7 to 11.1 mg/L; L-arginine*HCl from 6.7 to 8.5 mg/L; L-cystine*2HCl from 5.0 to 6.4 mg/L; L-glutamine from 47 to 59 mg/L; glycine from 2.4 to 3.0 mg/L; L-histidine*HCl*H$_2$O from 3.4 to 4.3 mg/L; L-isoleucine and L-leucine from 8.4 to 10.7 mg/L; L-lysine*HCl from 11.7 to 14.8 mg/L; L-methionine from 2.4 to 3.0 mg/L; L-phenylalanine from 5.3 to 6.7 mg/L; L-serine from 3.4 to 4.3 mg/L; L-threonine from 7.6 to 9.7 mg/L; L-tryptophan from 1.3 to 1.6 mg/L; L-tyrosine*2 Na*2H$_2$O from 9.6 to 12.2 mg/L; soy, wheat and yeast hydrolysates at 0.5 to 3 g/L; dextrane sulfate between 20 and 80 mg/L; myo-inositol from 0.58 to 0.73 mg/L; riboflavin from 0.03 to 0.04 mg/L; any or all of choline chloride, folic acid, niacinamide, D-pantothenic acid*½ Ca, pyridoxal*HCl, pyridoxine*HCl, and thiamine*HCl from 0.32 to 0.41 mg/L; HEPES from 476.64 to 605.33 mg/L; and pyruvate*Na from 8.8 to 11.2 mg/L.

A stable culture that proliferated in single-cell suspension without dependence on microcarriers could be maintained in chemically-defined medium at cell densities between 0.3× 10$^6$ and at least 10×10$^6$ cells/mL starting with week 16 (corresponding to passage 21). A stirred-tank bioreactor was inoculated out of this stable culture at passage 26, the culture was maintained for at least additional 8 weeks to demonstrate that adaptation has been accomplished. No animal-derived components and no trypsin was used after passage 5 and, therefore, was also not used towards inoculation of the bioreactor.

A culture stably adapted to proliferation in suspension in chemically defined medium free of animal-derived components was also obtained of the ST cell line. This cell line transiently required supplementation with 30-60 mg/L putrescine, 30-50 mg/L spermine, 5-25 µL/L TrypLE, 200 ng/mL insuline, 1-3 g/L soy hydrolysate, 0.05% methylcellulose, and 600-900 mg/L NaCl in addition to the components given above for full adaptation.

A continuous passage history in media free of animal derived components is highly desirable. Animal derived components, especially bovine serum, can be contaminated with adventitious agents that can cause disease in vaccine recipients and that complicate trans-boundary dissemination of vaccine preparations [46]. Cryocultures of the PK-15S and STS cell lines were submitted according to the Budapest Treaty to the DSMZ on Sep. 21, 2016 and received the deposit numbers DSM ACC3307 and DSM ACC3308, respectively. Both cryocultures were obtained out of cultures that proliferate in animal-derived component free medium (the medium for PK-15S is even chemically-defined), they were passaged at least 10 times in such medium, and they are stored in preservation medium free of animal-derived components.

In summary, a robust adaptation to continuous proliferation in medium free of animal derived components in true suspension is demonstrated for the PK-15 and ST cell lines for the first time.

1.2 Cell Line Identity and Purity

Cell line cross-contamination is a frequent problem. To confirm that the here described PK-15S cell line is pure, PCR was performed to examine cell identity.

Figure 2:
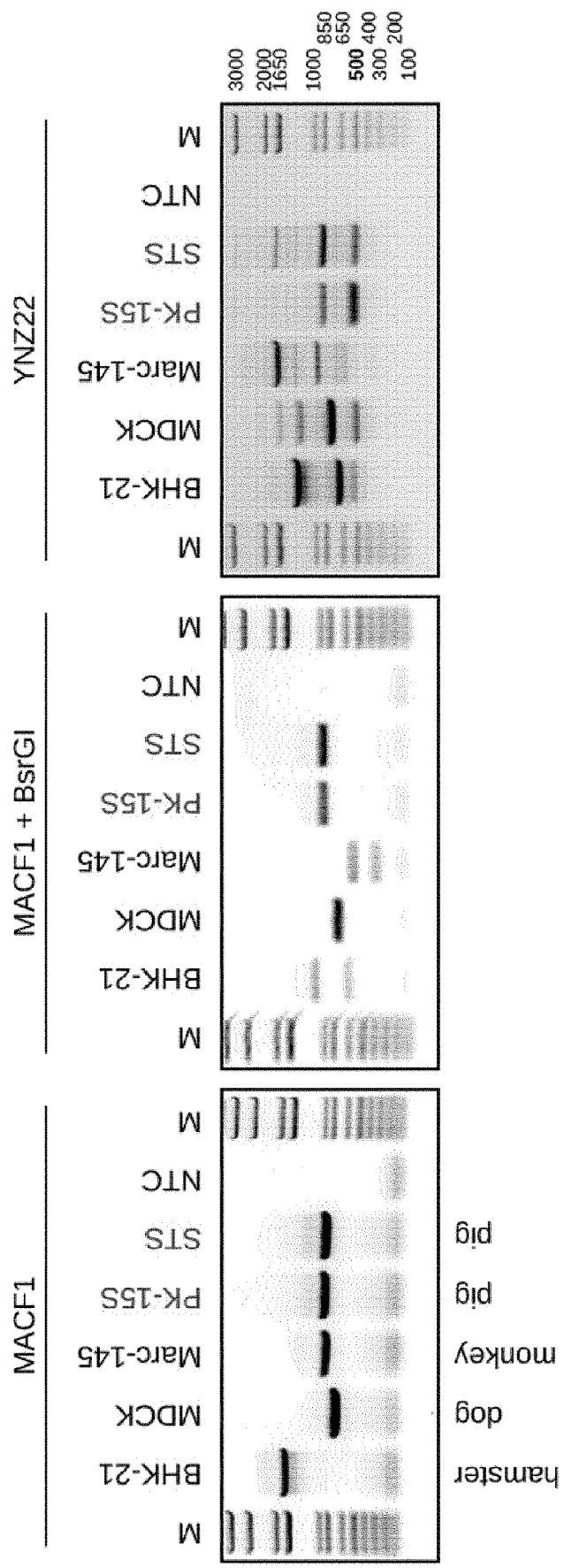
FIG. 2: Cell identities with expanded PCR analysis. MACF1 PCR described in [45] has been applied to different cell cultures. A BsrGI polymorphism allows differentiation of monkey (Marc-145) and swine (PK-15S and STS) that give otherwise similar amplification products. The simplicity of the MACF1 banding pattern allows identification of potential contaminations. The results presented here show that the cell lines are of expected identity and that no contamination has occurred, especially not between Marc-145 and PK-15S and not MDCK (another cell line permissive for AIV) and PK-15S. YNZ22 PCR furthermore allows to differentiate between cell lines of the same species origin, PK-15S and STS yield different signals.
Figure 3:
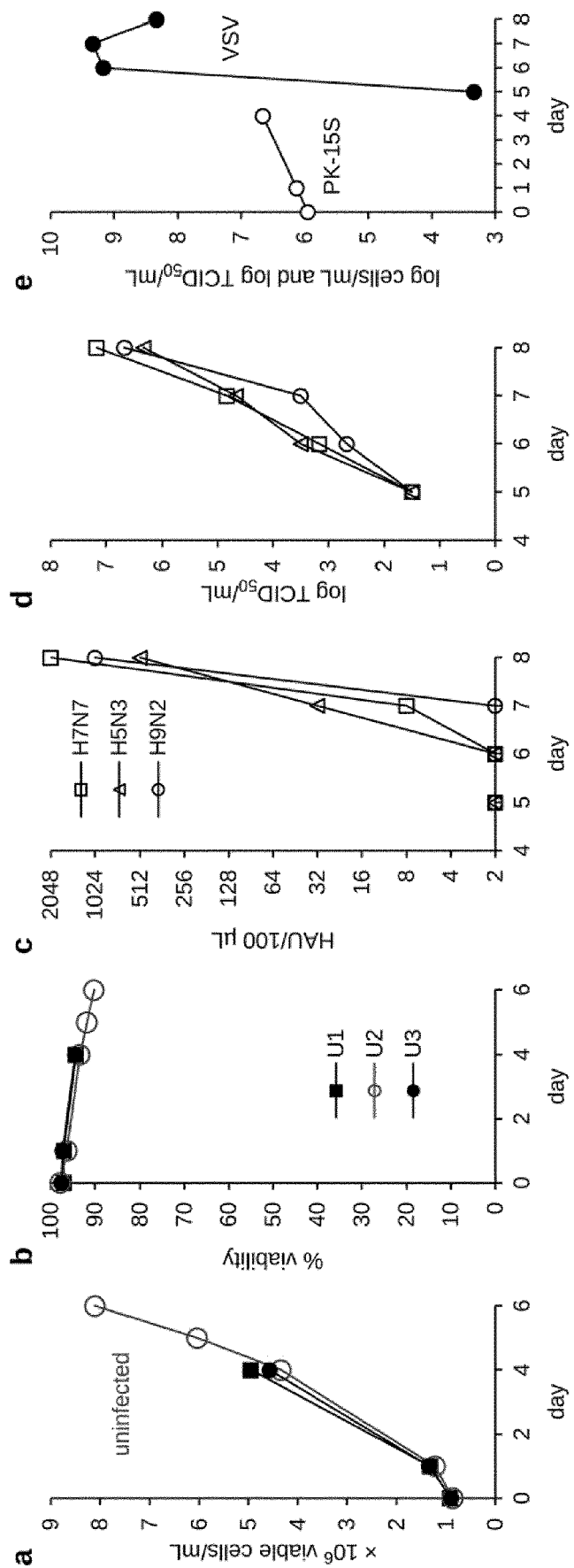
FIG. 3: Propagation of AIV in PK-15S suspension cultures in a stirred tank bioreactor. This experiment was performed with cells beyond passage 26 in single-cell suspension in chemically defined medium. Trypsin was used to activate the infectious activity of the LPAIVs and was added to 16 U/mL of culture volume per day. All LPAIVs were inoculated at a MOI of $10^{-4}$. (A) Cell proliferation in the stirred tank bioreactor. Infection was usually performed at day 4 at typical cell densities between 3 and $5 \times 10^6$ cells/mL. One bioreactor (open circle, red) was continued as reference without infection until day 6. Cell density was beyond $8 \times 10^6$ at day 6 for this uninfected bioreactor. (B) Viability was above 90% in most experiments, also in this one. The cultures shown here correspond to those shown in panel A. (C) HAU units and (D) infectious TCID50 units of LPAIV H5N3, H7N7 and H9N2. (E) Combined chart depicting cell proliferation and infectious units in a bioreactor infected with vesicular stomatitis virus (VSV, Rhabdoviridae). MOI in this experiment was $10^{-3}$.
Figure 4:
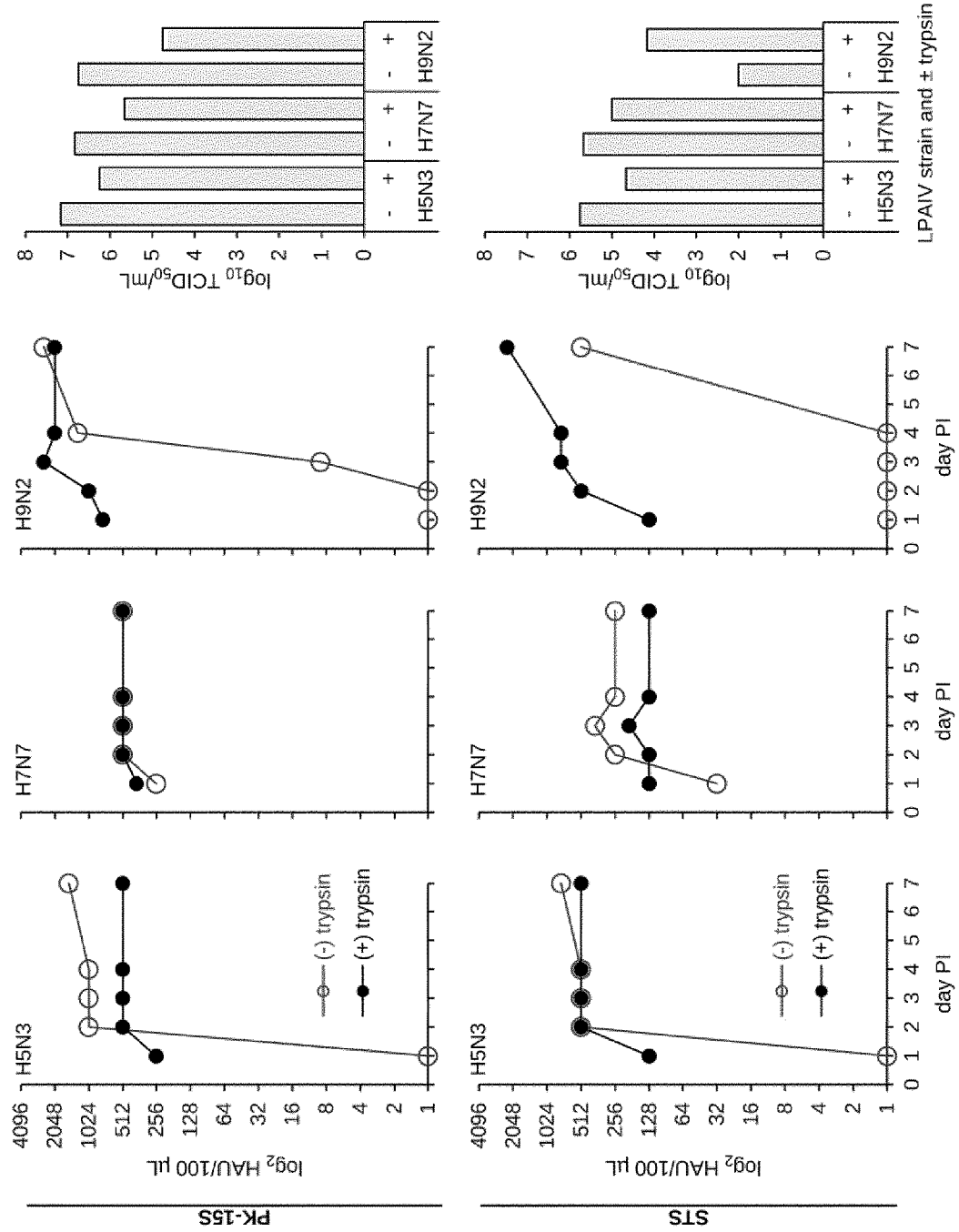
FIG. 4: PK-15 allows influenza virus propagation without exogenous protease addition. NDV also replicated in the here described porcine cells without addition of trypsin (data not shown, PK-15S). The bar graphs depict infectious titers at day 3.
Figure 5:
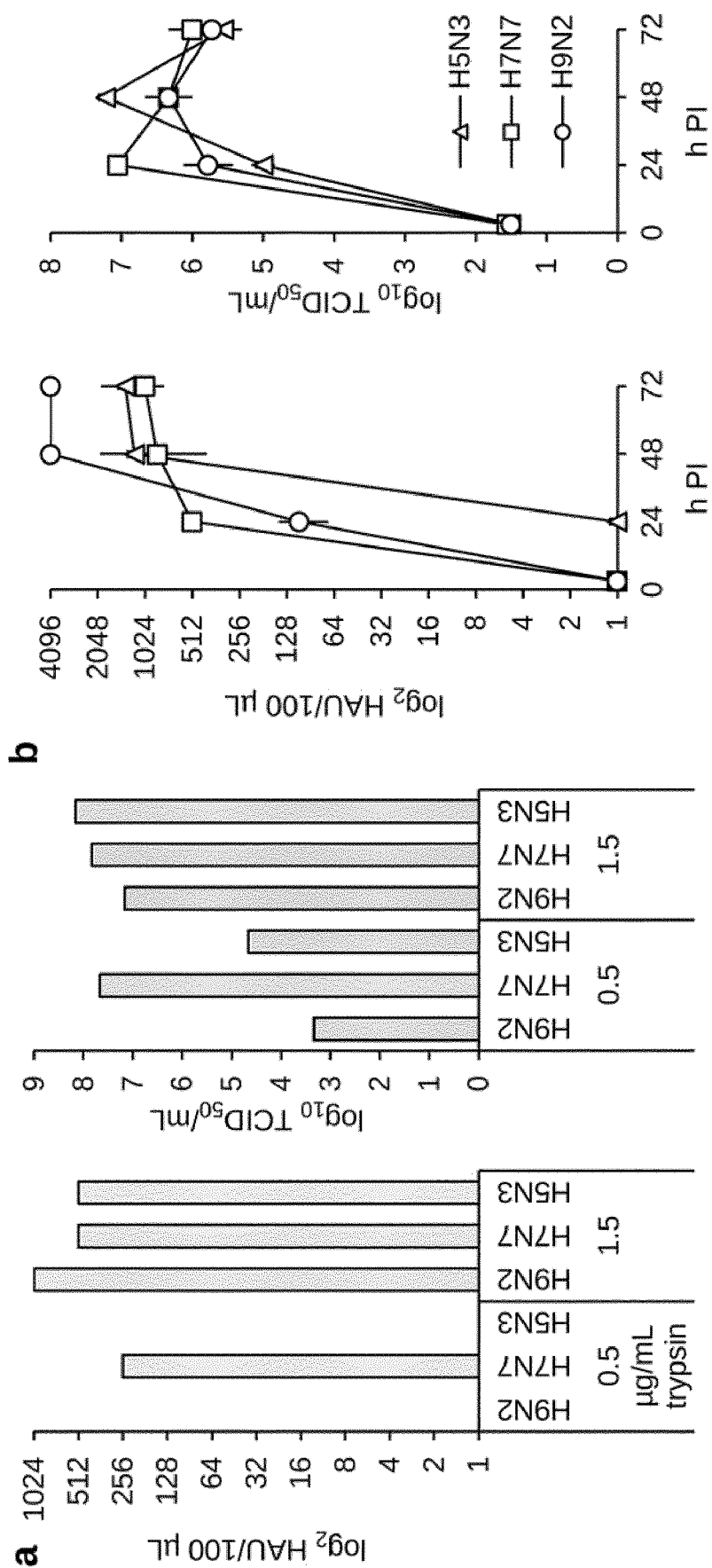
FIG. 5: Results obtained with the same viruses in MDCK suspension cultures in chemically defined medium CD-U5 supplemented for MDCK propagation. (A) Higher amounts of trypsin generally lead to higher infectious or hemagglutinating titers. Dependence on trypsin is confirmed further down. (B) Kinetic of LPAIV replication in MDCK suspension cultures. Note the strong decline of infectious units already 72 h post infection.

Fehler! Verweisquelle konnte nicht gefunden werden. FIG. 2 shows a refined assay for identity of the cell lines with DNA isolated out of the cultures that are intended to be transferred back to the originating laboratory. Purity and identity of the cultures to within the detection limit of this sensitive method is confirmed. A MACF1-assay that has been expanded to include a BsrGI restriction fragment length polymorphism allows a clear distinction between porcine and simian cells. A microsatellite assay allows to differentiate different cell lines from the same species (PK15 and ST).

The banding pattern in FIG. 2 was obtained as follows: DNA was isolated from $4 \times 10^6$ cells with QIAmp DNA Blood Mini columns (Qiagen) according to the manufacturer's instructions. PCRs were performed with 100 ng of template DNA and 2 µM of primer. Cycle parameters were 35 repeats of 55° C. annealing for 30 s, 72° C. extension for 180 s and 94° C. melting for 20 s. MACF1 primer sequences are CCATCTgCTgAgTATAAAgTggTgAA (SEQ ID NO: 1) and gCCTCCTTCTgCTTgAAgCA (SEQ ID NO: 2), single-primer PCR for amplification of YNZ22 minisatellites was performed with CTCTgggTgTCgTgC (SEQ ID NO: 3).

In summary, the here described PK-15S and STS cultures are pure and identifiable. Most importantly, the presence of simian or canine material was not observed, previously demonstrated to be highly permissive for influenza viruses, in PK-15S or STS cultures.

1.3 High Titers after Influenza Virus Infection

Orthomyxoviruses depend on proteolytic activation of the viral receptor, the HA protein, very similar to the paramyxoviruses [33-35]. The embryonal tissues provide the required proteases if vaccines are produced in embryonated eggs. The proteases contained in embryonated eggs are replaced by exogenous trypsin for production of myxovirus vaccines in cell cultures.

Influenza A viruses (AIVs) isolated with the help of cell lines have been proposed to be suitable as vaccine seeds [50]. Important parameters in the determination of vaccine properties are infectious units as an indicator for active viruses present in the preparations. Another important parameter is the haemagglutinating activity on erythrocyte preparations from chicken, horse or guinea pig as an indicator for the amount of potentially reactogenic antigen present in the vaccine harvest.

The hemagglutinating and infectious activities of at least three different low pathogenic Influenza A viruses (LPAIVs) propagated in the suspension PK-15S cells in true suspension cultures in chemically-defined medium without microcarriers and at extremely low MOIs compare favourably, or are even superior to the results reported in MDCK cells [50,51] or obtained here as reference and that are shown in FIG. 5.

The results shown in FIG. 3 were obtained as follows: Cells were maintained in CD-U4 (GE Healthcare #T1313) or CD-U5 medium (BD Biosciences #16ABP247) supplemented to 10 ng/mL with LONG R3IGF-I (Sigma #91590C) and 1× stable L-glutamine (such as GlutaMAX-I, Gibco #35050-038, alternatively 2 mM conventional glutamine). They were cultivated in 0.2 μm-vented 125 mL-flasks (Corning #431143) with 25-62 mL working volume or vented 50 mL-tubes (Tubespin Bioreactor 50, TPP #87050) with 5-15 mL working volume. Incubation was performed in INFORS HT Multitron Cell shaking incubator set to 36.5° C. and 8% $CO_2$, RPM is 150 for flasks and 180 for spin tubes, respectively, and amplitude or throw of the rotating platform is 5 cm.

The cells were subcultivated between $8\times10^5$ viable cells/mL and $6\times10^6$ viable cells/mL for routine passaging, usually with two splits per week. Subpassage was performed by at least 5-fold dilution of the cell suspension without any centrifugation.

Infectious titers of LPAIVs were determined on Vero cells. $1.5\times10^6$ cells in DMEM:F12 medium containing 2 mM GlutaMAX I (both Gibco) and 5% fetal calf serum (Biochrom) were seeded into CellBIND 96-well plates (Corning) at 100 μL of cell suspension. The medium was replaced on the following day against DMEM:F12 containing 2 mM GlutaMAX I and 1.5 μg/mL trypsin (type IX-S, Sigma T0303), but no fetal calf serum. Serial dilutions in steps of 10 of LPAIV-containing virus samples were prepared in DMEM:F12 medium free of serum, and 10 μL each of the dilutions were added to the Vero cultures. Virus replication was allowed at 37° C. for 72 h and detected by the cytopathic effect. Calculation of $TCID_{50}$ values was performed according to Spearman and Kärber using the implementation of the FAO [52, 53].

Haemagglutination units (HAU) were determined with chicken erythrocytes and serial dilutions of infected cell suspensions in PBS in steps of 2. Erythrocytes from 7 mL of a 25% complete blood suspension in Alsever buffer (E200, Labor Dr. Merk & Kollegen GmbH, Germany) were washed thrice in cold PBS and diluted in PBS to a concentration that yields an OD of 2.9 to 3.1 at 576 nm. This suspension was stored for up to one week at 4° C. Centrifugation for the washing steps was performed at room temperature with 500×g, brake set to low, for 5 min each.

The assay was performed in round-bottom 96-well microtiter plates. The first row of the plate was filled with 200 μL of the crude culture supernatant and all other rows received 100 μL of PBS. Next, 100 μL of virus sample was added to the second row, the pipetting tips were replaced and the suspension mixed with fresh tips. This two-fold dilution was continued serially into the next row, and, for samples with high potency, continued into a second plate. Each well thus contained 100 μL of diluted virus sample and was subsequently supplemented with 100 μL of the erythrocyte suspension. This volume was mixed by pipetting and the turbid solution allowed to stand undisturbed for 60 min at ambient temperature (22° C.). HAU/100 μL are given by the highest dilution where formation of the characteristic dot was not yet visible.

The bioreactor experiments were conducted in DASBox (DASGip, Eppendorf) bioreactor units. These stirred-tank reactors are equipped with a Marine impeller with 3 blades and 60-250 mL working-volume vessels. Gas mixing was performed with N2, air, $CO_2$ and $O_2$. The pH was adjusted with $CO_2$ and 1 M $Na_2CO_3$. Inoculation was performed to $0.8\times10^6$ PK-15S and $1\times10^6$ BHK cells/mL in CD-U4 medium and the culture was allowed to proliferate for 4 days to approximately $3\times10^6$ cells/mL. Glutamine was usually added to 2 mM at day 4 and glucose to 6 g/L at day 5. (see FIG. 3).

The parameters for the cell proliferation phase were 37° C. culture temperature, 60% DO (dissolved oxygen) saturation in the medium, 180 rpm for the impeller, and a pH 7.1. The pH was increased to 7.5 units as a gradient over 6 h after infection.

Trypsin (type IX-S, Sigma T0303) was added automatically to the infected culture to 16 U/mL of reactor volume per day in 4 burst of 4 mL each separated by 6 hours. This particular trypsin is provided as 1 g lyophylisate that was resuspended to 1 mg/mL in PBS. Specific activity depends on the lot and was 18500 U/mg in our experiments. Addition of 16 U/mL therefore corresponds to less than 0.9 µg/mL of trypsin which is well below the toxic level in the range of 2.5 µg/mL.

In summary, for the first time, a PK-15S cell line was demonstrated to allow production of LPAIV seed viruses to high infectious and haegglutinating titers in a stirred tank bioreactor in chemically defined medium. The results were at least as good as those obtained with MDCK.

1.4 Independent of Trypsin

The virions of many viruses such as ortho- and paramyxoviruses must be proteolytically processed for activation of the infectious units. The proteases contained in embryonated eggs are sufficient to activate influenza and Newcastle disease viruses. The addition or ectopical expression [54] of exogenous trypsin or other proteases is required for production of these viruses in cell cultures.

It would be highly advantageous, and very unusual, if a continuous cell line would allow production of influenza virus isolates independent of exogenously added trypsin and only with a natively inherent cognate protease activity. Such an inherent property may help in the identification and production of viruses, e.g. of low-pathogenic field isolates. Such a property is clearly different from the introduction of selected non-cognate proteases by genetic recombination.

To test for such a property requires a cell line that robustly proliferates in a medium as the here described chemically-defined cell proliferation medium with a very low protein content (10 ng/mL of recombinant IGF) and without other substances that may interfere with the enzymatic activity of proteases.

Infectious titers and HA titers of LPAIVs were determined as described above. Detection of NDV replication in the titration plates was facilitated by immunostaining: the Vero indicator cells were fixed in methanol for 10 min, allowed to dry to completion, and rehydrated with PBS containing 0.05% Tween-20. NDV antiserum (GD Animal Health) was added to a dilution of 1:2000 in PBS containing 1% fetal calf serum and incubated for 1 h at room temperature. After two washes with PBS, secondary antibody (anti-chicken, Alexa Fluor 488 labelled, host rabbit, Dianova, 303-545-003 at 1 μg/μL) was added at a dilution of 1:2000 for 2 h at ambient temperature or overnight at 4° C. Infected wells were identified by fluorescence after two washes with PBS.

The HA units were determined as described for LPAIVs above with one modification, titration was performed with sonicated, rather than crude cell lysate. Sonication was performed using a Vial Tweeter (set to 20 s of 100% cycle and 90% amplitude) that allows handling of closed sample caps to avoid cross-contamination (Hielscher, Germany).

The results are shown in FIGS. 4 and 5.

In summary, a cell culture system that does not require exogenous trypsin, and that allows propagation of LPAIVs to very high hemagglutinating and infectious titers has been developed.

1.5 the Protease in the Porcine Cell Lines is Endogenous

It has further been quantified whether the protease of the porcine cell lines is active intracellularly as has been described for human airway epithilium [55,56]. Serum contains a wide spectrum of high-molecular weight protease inhibitors [57] that would interfere with exogenous proteases (such as trypsin) or proteases that are being secreted by the host cell or contained in the vaccine preparation.

The data shown in FIG. 6 was obtained as follows: suspension cells were provided at a cell density of $2\times10^6$ cells/mL in chemically-defined medium. Bovine serum was added to a concentration of 2% 2 h prior to infection. Next, the CR.pIX and MDCK cell lines that were previously shown to allow propagation of influenza viruses only in presence of trypsin were given the protease, the porcine cell lines were examined always in absence of trypsin. LPAIV H5N3 was added to a MOI of $10^{-4}$ and titers were determined 3 days PI. CR.pIX and MDCK positive controls consisted of reactions without serum but with trypsin, and negative controls of reactions without serum and trypsin.

FIG. 6 demonstrates that exogenous trypsin is required for propagation of influenza viruses in the avian and canine cell lines. Furthermore, this trypsin supplementation is being quenched by addition of serum. This observation is in stark contrast to the phenomenon that influenza viruses replicate to high titers also without trypsin and in the presence of bovine serum in PK-15S and STS. The high-molecular weight protease inhibitors present in serum cannot enter the cell. This experiment, therefore, demonstrates the activity of an endogenous intracellular protease capable of activating LPAIVs in cultures of PK-15S and STS.

That the endogenous activity is unusually high in the PK-15S and STS cell lines in combination with the suspension culture format and in medium free of animal derived components can be inferred from the high susceptibility and high permissivity. For example, the infectious yield for any of the tested strains (H5N3, H7N7 or M9N2) in PK-15S was at least $10^6$ $TCID_{50}$/mL, the MOI was $10^{-4}$ viruses/cell, and cell density was $2\times10^6$ cells/mL. The input was, thus, of $(2\times10^6$ cells/mL$)\times(10^{-4}$ $TCID_{50}$/cell$)=200$ $TCID_{50}$/mL. The burst size was ($10^6$ $TCID^{50}$/mL): (200 $TCID_{50}$/mL)=5000. A burst size higher than 100 demonstrates high permissivity and that productive infection with such a burst size is obtained with a MOI of only $10^{-4}$, 10-fold below 0.001, demonstrates high susceptibility.

An unusually broad investigation has been presented that includes industrially relevant avian, canine and porcine cell lines. The data shown in FIG. 6 clearly demonstrates that only the hitherto undescribed advantageous combination of chemically defined medium, metabolically or genomically shifted porcine cell line and suspension culture format allows for robust production of myxoviruses without addition of exogenous trypsin and animal-derived supplements.

REFERENCES

1. Richard, M.; de Graaf, M.; Herfst, S. Avian influenza A viruses: from zoonosis to pandemic. *Future Virol.* 2014, 9, 513-524.
2. Li, F. C. K.; Choi, B. C. K.; Sly, T.; Pak, A. W. P. Finding the real case-fatality rate of H5N1 avian influenza. *J. Epidemiol. Community Health* 2008, 62, 555-559.
3. Sonnberg, S.; Webby, R. J.; Webster, R. G. Natural history of highly pathogenic avian influenza H5N1. *Virus Res.* 2013, 178, 63-77.
4. Simon-Grifé, M.; Martin-Valls, G. E.; Vilar, M. J.; Busquets, N.; Mora-Salvatierra, M.; Bestebroer, T. M.; Fouchier, R. A.; Martin, M.; Mateu, E.; Casal, J. Swine influenza virus infection dynamics in two pig farms; results of a longitudinal assessment. *Vet. Res.* 2012, 43, 24.
5. Ma, W.; García-Sastre, A.; Schwemmle, M. Expected and Unexpected Features of the Newly Discovered Bat Influenza A-like Viruses. *PLoS Pathog.* 2015, 11, e1004819.
6. Hause, B. M.; Collin, E. A.; Liu, R.; Huang, B.; Sheng, Z.; Lu, W.; Wang, D.; Nelson, E. A.; Li, F. Characterization of a novel influenza virus in cattle and Swine: proposal for a new genus in the Orthomyxoviridae family. *mBio* 2014, 5, e00031-00014.
7. Kobasa, D.; Jones, S. M.; Shinya, K.; Kash, J. C.; Copps, J.; Ebihara, H.; Hatta, Y.; Kim, J. H.; Halfmann, P.; Hata, M.; Feldmann, F.; Alimonti, J. B.; Fernando, L.; Li, Y.; Katze, M. G.; Feldmann, H.; Kawaoka, Y. Aberrant innate immune response in lethal infection of macaques with the 1918 influenza virus. *Nature* 2007, 445, 319-323.
8. Gambotto, A.; Barratt-Boyes, S. M.; de Jong, M. D.; Neumann, G.; Kawaoka, Y. Human infection with highly pathogenic H5N1 influenza virus. *Lancet* 2008, 371, 1464-1475.
9. Ma, W.; Kahn, R. E.; Richt, J. A. The pig as a mixing vessel for influenza viruses: Human and veterinary implications. *J. Mol. Genet. Med. Int. J. Biomed. Res.* 2008, 3, 158-166.
10. Bano, S.; Naeem, K.; Malik, S. A. Evaluation of pathogenic potential of avian influenza virus serotype H9N2 in chickens. *Avian Dis.* 2003, 47, 817-822.
11. Sun, Y.; Liu, J. H9N2 influenza virus in China: a cause of concern. *Protein Cell* 2015, 6, 18-25.
12. Monne, I.; Hussein, H. A.; Fusaro, A.; Valastro, V.; Hamoud, M. M.; Khalefa, R. A.; Dardir, S. N.; Radwan, M. I.; Capua, I.; Cattoli, G. H9N2 influenza A virus circulates in H5N1 endemically infected poultry population in Egypt. *Influenza Other Respir. Viruses* 2013, 7, 240-243.
13. Wan, H.; Sorrell, E. M.; Song, H.; Hossain, M. J.; Ramirez-Nieto, G.; Monne, I.; Stevens, J.; Cattoli, G.; Capua, I.; Chen, L.-M.; Donis, R. O.; Busch, J.; Paulson, J. C.; Brockwell, C.; Webby, R.; Blanco, J.; Al-Natour, M. Q.; Perez, D. R. Replication and transmission of H9N2 influenza viruses in ferrets: evaluation of pandemic potential. *PLoS One* 2008, 3, e2923.
14. Wan, H.; Perez, D R Amino acid 226 in the hemagglutinin of H9N2 influenza viruses determines cell tropism and replication in human airway epithelial cells. *J. Virol.* 2007, 81, 5181-5191.
15. Ito, T.; Couceiro, J. N.; Kelm, S.; Baum, L. G.; Krauss, S.; Castrucci, M. R.; Donatelli, I.; Kida, H.; Paulson, J. C.; Webster, R. G.; Kawaoka, Y. Molecular basis for the generation in pigs of influenza A viruses with pandemic potential. *J. Virol.* 1998, 72, 7367-7373.
16. Sheta, B. M.; Fuller, T. L.; Larison, B.; Njabo, K. Y.; Ahmed, A. S.; Harrigan, R.; Chasar, A.; Abdel Aziz, S.; Khidr, A.-A. A.; Elbokl, M. M.; Habbak, L. Z.; Smith, T. B. Putative human and avian risk factors for avian influenza virus infections in backyard poultry in Egypt. *Vet. Microbiol.* 2014, 168, 208-213.
17. Capua, I.; Marangon, S. Control of avian influenza in poultry. *Emerg. Infect. Dis.* 2006, 12, 1319-1324.
18. Swayne, D.; Brown, I. Chapter 2.3.4. Avian Influenza. *OIE Man. Diagn. Tests Vaccines Terr. Anim.* 2015, 1, 436-454.
19. Ackland, N. R.; Tannock, G. A.; Young, I. F. A device for the nondestructive decontamination of large volumes of infected egg waste. *Appl. Environ. Microbiol.* 1985, 49, 920-924.
20. Enserink, M. Influenza. Crisis underscores fragility of vaccine production system. *Science* 2004, 306, 385.
21. Hoa, L. K.; Hiep, L. V.; Be, L. V. Development of pandemic influenza vaccine production capacity in Viet Nam. *Vaccine* 2011, 29 Suppl 1, A34-36.
22. Sambo, E.; Bettridge, J.; Dessie, T.; Amare, A.; Habte, T.; Wigley, P.; Christley, R. M. Participatory evaluation of chicken health and production constraints in Ethiopia. *Prev. Vet. Med.* 2015, 118, 117-127.
23. Osterrieder, N.; Schumacher, D. A continuous cell line for the production of vaccines. WO/2003/066093 A1. 2002.
24. Uscher-Pines, L.; Barnett, D. J.; Sapsin, J. W.; Bishai, D. M.; Balicer, R. D. A systematic analysis of influenza vaccine shortage policies. *Public Health* 2008, 122, 183-191.
25. Chua, J. V.; Chen, W. H. Bench-to-bedside review: vaccine protection strategies during pandemic flu outbreaks. *Crit. Care Lond. Engl.* 2010, 14, 218.
26. Böni, J.; Stalder, J.; Reigel, F.; Schüpbach, J. Detection of reverse transcriptase activity in live attenuated virus vaccines. *Clin. Diagn. Virol.* 1996, 5, 43-53.
27. David, S. A. W.; Volokhov, D. V.; Ye, Z.; Chizhikov, V. Evaluation of Mycoplasma inactivation during production of biologics: egg-based viral vaccines as a model. *Appl. Environ. Microbiol.* 2010, 76, 2718-2728.
28. Doroshenko, A.; Halperin, S. A. Trivalent MDCK cell culture-derived influenza vaccine Optaflu (Novartis Vaccines). *Expert Rev. Vaccines* 2009, 8, 679-688.
29. Gregersen, J.-P.; Schmitt, H.-J.; Trusheim, H.; Bröker, M. Safety of MDCK cell culture-based influenza vaccines. *Future Microbiol.* 2011, 6, 143-152.
30. Parvin, R.; Shehata, A. A.; Heenemann, K.; Gac, M.; Rueckner, A.; Halami, M. Y.; Vahlenkamp, T. W. Differential replication properties among H9N2 avian influenza viruses of Eurasian origin. *Vet. Res.* 2015, 46, 75.
31. Trombetta, C.; Piccirella, S.; Perini, D.; Kistner, O.; Montomoli, E. Emerging Influenza Strains in the Last Two Decades: A Threat of a New Pandemic? *Vaccines* 2015, 3, 172-185.
32. Skowronski, D. M.; Janjua, N. Z.; De Serres, G.; Sabaiduc, S.; Eshaghi, A.; Dickinson, J. A.; Fonseca, K.; Winter, A.-L.; Gubbay, J. B.; Krajden, M.; Petrie, M.; Charest, H.; Bastien, N.; Kwindt, T. L.; Mahmud, S. M.; Van Caeseele, P.; Li, Y. Low 2012-13 influenza vaccine effectiveness associated with mutation in the egg-adapted H3N2 vaccine strain not antigenic drift in circulating viruses. *PLoS One* 2014, 9, e92153.
33. Zhirnov, O. P.; Ovcharenko, A. V.; Bukrinskaya, A. G. Myxovirus replication in chicken embryos can be suppressed by aprotinin due to the blockage of viral glycoprotein cleavage. *J. Gen. Virol.* 1985, 66 (Pt 7), 1633-1638.
34. Muramatsu, M.; Homma, M. Trypsin action on the growth of Sendai virus in tissue culture cells. V. An activating enzyme for Sendai virus in the chorioallantoic fluid of the embryonated chicken egg. *Microbiol. Immunol.* 1980, 24, 113-122.
35. Rott, R.; Reinacher, M.; Orlich, M.; Klenk, H. D. Cleavability of hemagglutinin determines spread of avian influenza viruses in the chorioallantoic membrane of chicken embryo. *Arch. Virol.* 1980, 65, 123-133.
36. Garten, W.; Bosch, F. X.; Linder, D.; Rott, R.; Klenk, H. D. Proteolytic activation of the influenza virus hemagglutinin: The structure of the cleavage site and the enzymes involved in cleavage. *Virology* 1981, 115, 361-374.

37. Nagai, Y.; Shimokata, K.; Yoshida, T.; Hamaguchi, M.; Iinuma, M.; Maeno, K.; Matsumoto, T.; Klenk, H. D.; Rott, R. The spread of a pathogenic and an apathogenic strain of Newcastle disease virus in the chick embryo as depending on the protease sensitivity of the virus glycoproteins. *J. Gen. Virol.* 1979, 45, 263-272.

38. Steinhauer, D. A. Role of hemagglutinin cleavage for the pathogenicity of influenza virus. *Virology* 1999, 258, 1-20.

39. Gong, W.; Zhang, L.; Lu, Z.; Jia, J.; Wang, M.; Peng, Z.; Guo, H.; Shi, J.; Tu, C. Complete genome sequence of a novel sub-subgenotype 2.1 g isolate of classical swine fever virus from China. *Arch. Virol.* 2016.

40. Delrue, I.; Van Gorp, H.; Van Doorsselaere, J.; Delputte, P. L.; Nauwynck, H. J. Susceptible cell lines for the production of porcine reproductive and respiratory syndrome virus by stable transfection of sialoadhesin and CD163. *BMC Biotechnol.* 2010, 10, 48.

41. Ma, C.; Song, H.; Guan, K.; Zhou, J.; Xia, X.; Li, F. Characterization of swine testicular cell line as immature porcine Sertoli cell line. *In Vitro Cell. Dev. Biol. Anim.* 2016, 52, 427-433.

42. Li, I. W. S.; Chan, K. H.; To, K. W. K.; Wong, S. S. Y.; Ho, P. L.; Lau, S. K. P.; Woo, P. C. Y.; Tsoi, H. W.; Chan, J. F. W.; Cheng, V. C. C.; Zheng, B. J.; Chen, H.; Yuen, K. Y. Differential susceptibility of different cell lines to swine-origin influenza A H1N1, seasonal human influenza A H1N1, and avian influenza A H5N1 viruses. *J. Clin. Virol. Off. Publ. Pan Am. Soc. Clin. Virol.* 2009, 46, 325-330.

43. Herman, M.; Haugerud, S.; Malik, Y. S.; Goyal, S. M. Improved in vitro cultivation of swine influenza virus. *Int J Appl Res Vet Med* 2005, 3, 124-128.

44. Ngunjiri, J. M.; Mohni, K. N.; Sekellick, M. J.; Schultz-Cherry, S.; Webster, R. G.; Marcus, P. I. Lethal H5N1 influenza viruses are not resistant to interferon action in human, simian, porcine or chicken cells. *Nat. Med.* 2012, 18, 1456-1457.

45. Jordan, I.; Munster, V. J.; Sandig, V. Authentication of the R06E fruit bat cell line. *Viruses* 2012, 4, 889-900.

46. Hawkes, P. W. Fetal bovine serum: geographic origin and regulatory relevance of viral contamination. *Bioresour. Bioprocess.* 2015, 2, 1.

47. Rodrigues, M. E.; Costa, A. R.; Henriques, M.; Cunnah, P.; Melton, D. W.; Azeredo, J.; Oliveira, R. Advances and drawbacks of the adaptation to serum-free culture of CHO-K1 cells for monoclonal antibody production. *Appl. Biochem. Biotechnol.* 2013, 169, 1279-1291.

48. Silva, A. C.; Delgado, I.; Sousa, M. F. Q.; Carrondo, M. J. T.; Alves, P. M. Scalable culture systems using different cell lines for the production of Peste des Petits ruminants vaccine. *Vaccine* 2008, 26, 3305-3311.

49. de la Luz-Hernández, K. R.; Rojas-del Calvo, L.; Rabasa-Legon, Y.; Lage-Castellanos, A.; Castillo-Vitlloch, A.; Díaz, J.; Gaskell, S. Metabolic and proteomic study of NSO myeloma cell line following the adaptation to protein-free medium. *J. Proteomics* 2008, 71, 133-147.

50. Donis, R. O.; Influenza Cell Culture Working Group; Influenza Cell Culture Working Group; Davis, C. T.; Foust, A.; Hossain, M. J.; Johnson, A.; Klimov, A.; Loughlin, R.; Xu, X.; Tsai, T.; Blayer, S.; Trusheim, H.; Colegate, T.; Fox, J.; Taylor, B.; Hussain, A.; Barr, I.; Baas, C.; Louwerens, J.; Geuns, E.; Lee, M.-S.; Venhuizen, O.; Neumeier, E.; Ziegler, T. Performance characteristics of qualified cell lines for isolation and propagation of influenza viruses for vaccine manufacturing. *Vaccine* 2014, 32, 6583-6590.

51. Ren, Z.; Lu, Z.; Wang, L.; Huo, Z.; Cui, J.; Zheng, T.; Dai, Q.; Chen, C.; Qin, M.; Chen, M.; Yang, R. Rapid production of a H9N 2 influenza vaccine from MDCK cells for protecting chicken against influenza virus infection. *Appl. Microbiol. Biotechnol.* 2015, 99, 2999-3013.

52. Bross, I. Estimates of the LD50; a critique. *Biometrics* 1950, 6, 413-423.

53. Litamoi, J.; Palya, V. J.; Sylla, D.; Rweyemamu, M. M. Quality control testing of contagious bovine pleuropneumonia live attenuated vaccine. Standard operating procedure 2: Estimation of viable *Mycoplasma* Content of CBPP Vaccines (Microtitration Method). Website: fao.org/docrep/003/v9952e00.htm (accessed April 2015). *FAO Anim. Prod. Health Pap.* 1996, 128.

54. Böttcher, E.; Freuer, C.; Steinmetzer, T.; Klenk, H.-D.; Garten, W. MDCK cells that express proteases TMPRSS2 and HAT provide a cell system to propagate influenza viruses in the absence of trypsin and to study cleavage of HA and its inhibition. Vaccine 2009, 27, 6324-6329.

55. Böttcher, E.; Matrosovich, T.; Beyerle, M.; Klenk, H.-D.; Garten, W.; Matrosovich, M. Proteolytic activation of influenza viruses by serine proteases TMPRSS2 and HAT from human airway epithelium. *J. Virol.* 2006, 80, 9896-9898.

56. Zhirnov, O. P.; Ikizler, M. R.; Wright, P. F. Cleavage of influenza a virus hemagglutinin in human respiratory epithelium is cell associated and sensitive to exogenous antiproteases. *J. Virol.* 2002, 76, 8682-8689.

57. Travis, J.; Salvesen, G. S. Human plasma proteinase inhibitors. *Annu. Rev. Biochem.* 1983, 52, 655-709.

---

The invention claimed is:

1. A continuous and non-adherent kidney or testis porcine cell line that is capable of proliferating in medium free of animal-derived components, wherein the cell line comprises an endogenous protease for activation of virus infectivity, wherein the cell line is infected with a virus or transfected with a plasmid carrying (a) nucleic acid sequence(s) encoding a virus, and wherein the virus carries a protease cleavage site cleavable by said endogenous protease, and wherein the virus is a virus of the Orthomyxoviridae or Paramyxoviridae family.

2. The continuous porcine cell line of claim 1, wherein the cell line is porcine kidney-15S (PK-15S).

3. The continuous porcine cell line of claim 2, wherein the cell line is deposited at the DSMZ with the deposit number DSM ACC3307.

4. The continuous porcine cell line of claim 1, wherein the cell line is swine testis S (STS).

5. The continuous porcine cell line of claim 4, wherein the cell line is deposited at the DSMZ with the deposit number DSM ACC3308.

6. The continuous porcine cell line of claim 1, wherein the virus is an influenza virus or Newcastle disease virus.

7. A method for producing a virus comprising the steps of:

providing a continuous and non-adherent porcine kidney or testis cell line that is capable of proliferating in medium free of animal-derived components and that is permissive for the virus, wherein the cell line comprises an endogenous protease for activation of virus infectivity, (ii) infecting said cell line with the virus or transfecting said cell line with a plasmid carrying (a) nucleic acid sequence(s) encoding the virus, and (iii) culturing the cell line infected or transfected in step (ii), thereby producing the virus, wherein the virus carries a protease cleavage site cleavable by said endogenous protease, and wherein the virus is a virus of the Orthomyxoviridae or Paramyxoviridae family.

8. The method of claim 7, which does not require the addition of an exogenous protease for activation of virus infectivity.

9. The method of claim 7, wherein the cell line is PK-15S.

10. The method of claim 9, wherein the cell line is deposited at the DSMZ with the deposit number DSM ACC3307.

11. The method of claim 7, wherein the cell line is STS.

12. The method of claim 11, wherein the cell line is deposited at the DSMZ with the deposit number DSM ACC3308.

13. The method of claim 7, wherein the virus is an influenza virus or Newcastle disease virus.

14. A continuous and non-adherent porcine cell line that is capable of proliferating in medium free of animal-derived components, wherein the cell line is deposited at the DSMZ with the deposit number DSM ACC3307.

15. A continuous and non-adherent porcine cell line that is capable of proliferating in medium free of animal-derived components, wherein the cell line is deposited at the DSMZ with the deposit number DSM ACC3308.

16. A method for producing a virus comprising the steps of:

(i) providing a continuous and non-adherent porcine cell line that is capable of proliferating in medium free of animal-derived components and that is permissive for a virus, (ii) infecting said cell line with the virus or transfecting said cell line with a plasmid carrying (a) nucleic acid sequence(s) encoding the virus, and (iii) culturing the cell line infected or transfected in step (ii), thereby producing the virus, wherein the cell line is deposited at the DSMZ with the deposit number DSM ACC3307.

17. A method for producing a virus comprising the steps of:

(i) providing a continuous and non-adherent porcine cell line that is capable of proliferating in medium free of animal-derived components and that is permissive for a virus, (ii) infecting said cell line with the virus or transfecting said cell line with a plasmid carrying (a) nucleic acid sequence(s) encoding the virus, and (iii) culturing the cell line infected or transfected in step (ii), thereby producing the virus, wherein the cell line is deposited at the DSMZ with the deposit number DSM ACC3308.

* * * * *